US009717555B2

(12) United States Patent
Chan et al.

(10) Patent No.: US 9,717,555 B2
(45) Date of Patent: Aug. 1, 2017

(54) CATHETER WITH HELICAL END SECTION FOR VESSEL ABLATION

(71) Applicant: BIOSENSE WEBSTER (ISRAEL), LTD., Yokneam (IL)

(72) Inventors: Tina Chan, El Monte, CA (US); Tom A. Ditter, Chino Hills, CA (US); Kristine Fuimaono, Covina, CA (US); Debby Grunewald, Los Angeles, CA (US); Eduardo Jimenez, Paramount, CA (US); Robert W. Pike, Coto De Caza, CA (US); Michael O. Zirkle, Yorba Linda, CA (US)

(73) Assignee: BIOSENSE WEBSTER (ISRAEL), LTD., Yokneam (IL)

( * ) Notice: Subject to any disclaimer, the term of this patent is extended or adjusted under 35 U.S.C. 154(b) by 0 days.

(21) Appl. No.: 13/826,698

(22) Filed: Mar. 14, 2013

(65) Prior Publication Data

US 2013/0304062 A1     Nov. 14, 2013

Related U.S. Application Data

(60) Provisional application No. 61/646,688, filed on May 14, 2012.

(51) Int. Cl.
*A61B 18/14*     (2006.01)
*A61B 17/00*     (2006.01)
*A61B 18/00*     (2006.01)

(52) U.S. Cl.
CPC ... *A61B 18/1492* (2013.01); *A61B 2017/00053* (2013.01); *A61B 2017/00738* (2013.01);
(Continued)

(58) Field of Classification Search
CPC ...... A61B 18/1492; A61B 2018/00351; A61B 2018/00375; A61B 2018/00577;
(Continued)

(56) References Cited

U.S. PATENT DOCUMENTS 4,488,561 A * 12/1984 Doring .................... 607/125
4,917,102 A * 4/1990 Miller et al. ............ 600/585
(Continued)

FOREIGN PATENT DOCUMENTS

CN    101766502 A    7/2010
CN    102000379 A    4/2011
(Continued)

OTHER PUBLICATIONS

European Search Report completed Aug. 14, 2013 for corresponding Patent Application No. EP13167733.
(Continued)

*Primary Examiner* — Jocelyn D Ram
(74) *Attorney, Agent, or Firm* — Roberts Mlotkowski Safran Cole & Calderon, P.C.

(57) ABSTRACT

A catheter includes an elongated body, a distal assembly with a shape-memory member defining a generally helical form, and a control handle. The control handle may be adapted to actuate a deflection puller wire for deflecting a portion of the elongated body and a contraction wire for contracting the generally helical form. The generally helical form carries irrigated ablation ring electrodes. A nitinol support member with shape memory extends through the distal assembly and into the elongated body to provide the helical form. The support member may have a varying stiffness along its length, for example, a decreasing stiffness toward a distal end of the support member. The support member can also be hollow so that it can receive a mandrel whose stiffness is greater than that of the support member.

34 Claims, 22 Drawing Sheets

(52) U.S. Cl.
CPC .............. *A61B 2017/00867* (2013.01); *A61B 2017/00955* (2013.01); *A61B 2018/0016* (2013.01); *A61B 2018/00029* (2013.01); *A61B 2018/00166* (2013.01); *A61B 2018/00214* (2013.01); *A61B 2018/00577* (2013.01); *A61B 2018/00642* (2013.01); *A61B 2018/00702* (2013.01); *A61B 2018/00821* (2013.01); *A61B 2018/1435* (2013.01); *A61B 2018/1467* (2013.01); *A61B 2018/1475* (2013.01); *A61B 2018/1497* (2013.01)

(58) Field of Classification Search
CPC .... A61B 2018/1435; A61B 2018/1467; A61B 2017/00867; A61B 2018/00511
USPC ................................ 606/41, 49; 604/530, 20
See application file for complete search history.

(56) References Cited

U.S. PATENT DOCUMENTS

| | | | | |
|---|---|---|---|---|
| 5,680,860 | A * | 10/1997 | Imran | 600/374 |
| 5,913,854 | A * | 6/1999 | Maguire et al. | 606/41 |
| 5,938,694 | A * | 8/1999 | Jaraczewski et al. | 607/122 |
| 5,964,757 | A | 10/1999 | Ponzi | |
| 6,002,955 | A * | 12/1999 | Willems et al. | 600/374 |
| 6,064,902 | A | 5/2000 | Haissaguerre et al. | |
| 6,371,955 | B1 | 4/2002 | Fuimaono et al. | |
| 6,468,260 | B1 | 10/2002 | Bumbalough et al. | |
| 6,500,167 | B1 | 12/2002 | Webster, Jr. | |
| 6,522,933 | B2 | 2/2003 | Nguyen | |
| 6,669,692 | B1 * | 12/2003 | Nelson et al. | 606/41 |
| 6,987,995 | B2 * | 1/2006 | Drysen | 600/374 |
| 7,276,061 | B2 * | 10/2007 | Schaer et al. | 607/41 |
| 8,066,702 | B2 * | 11/2011 | Rittman et al. | 606/41 |
| 9,220,433 | B2 * | 12/2015 | Ditter | A61B 18/1492 |
| 9,220,868 | B2 * | 12/2015 | Schultz | A61M 25/0147 |
| 2001/0007070 | A1 | 7/2001 | Stewart et al. | 606/41 |
| 2002/0169444 | A1 * | 11/2002 | Mest et al. | 606/41 |
| 2005/0033135 | A1 | 2/2005 | Govari | |
| 2006/0106295 | A1 * | 5/2006 | Jais et al. | 600/374 |
| 2006/0241366 | A1 * | 10/2006 | Falwell | A61B 5/0422 600/374 |
| 2007/0129761 | A1 | 6/2007 | Demarais et al. | |
| 2008/0161774 | A1 * | 7/2008 | Hastings et al. | 604/524 |
| 2008/0161803 | A1 * | 7/2008 | Oral et al. | 606/41 |
| 2010/0168548 | A1 * | 7/2010 | Govari et al. | 600/374 |
| 2010/0222851 | A1 | 9/2010 | Deem et al. | |
| 2011/0054287 | A1 | 3/2011 | Schultz | |
| 2011/0054446 | A1 * | 3/2011 | Schultz | 604/528 |
| 2011/0118582 | A1 * | 5/2011 | De la Rama et al. | 600/374 |
| 2011/0160719 | A1 * | 6/2011 | Govari et al. | 606/41 |
| 2011/0306851 | A1 * | 12/2011 | Wang | A61B 5/4893 600/301 |
| 2012/0116200 | A1 * | 5/2012 | Roy et al. | 600/374 |
| 2012/0116382 | A1 * | 5/2012 | Ku | A61B 18/1492 606/33 |
| 2012/0172703 | A1 | 7/2012 | Esguerra et al. | |
| 2012/0245577 | A1 * | 9/2012 | Mihalik et al. | 606/33 |
| 2012/0323174 | A1 * | 12/2012 | Shih | 604/95.04 |
| 2013/0006238 | A1 | 1/2013 | Ditter et al. | |
| 2013/0304047 | A1 * | 11/2013 | Grunewald | A61B 18/1492 606/14 |
| 2013/0304061 | A1 * | 11/2013 | Chang | A61B 18/1492 606/41 |
| 2013/0304062 | A1 * | 11/2013 | Chan et al. | 606/41 |
| 2014/0249525 | A1 * | 9/2014 | Scheib | A61B 18/1492 606/41 |
| 2015/0265345 | A1 * | 9/2015 | Bui | A61B 5/042 600/374 |

FOREIGN PATENT DOCUMENTS

| | | |
|---|---|---|
| CN | 202020532 U | 11/2011 |
| CN | 102846374 A | 1/2013 |
| EP | 2263588 | 12/2010 |
| EP | 2380518 | 10/2011 |
| EP | 2263588 A3 | 7/2012 |
| EP | 2 540 245 A1 | 1/2013 |

OTHER PUBLICATIONS

Biosense Webster (Israel), Ltd. U.S. Appl. No. 12/345,720—pending.
Biosense Webster (Israel), Ltd. U.S. Appl. No. 12/550,204—pending.
Biosense Webster (Israel), Ltd. U.S. Appl. No. 12/550,307—pending.
Biosense Webster (Israel), Ltd. U.S. Appl. No. 12/982,765—pending.
Biosense Webster (Israel), Ltd. U.S. Appl. No. 13/174,742—pending.
European Exam Report dated Nov. 25, 2014 from corresponding European Patent Application No. 13167733.8.
European Examination Report dated Apr. 21, 2016 in corresponding Application No. EP 14174792.3, 6 pages.
SIPO Office action dated Apr. 27, 2016 in corresponding CN application No. 201310176320.8, with English translation, 20 pages.

* cited by examiner

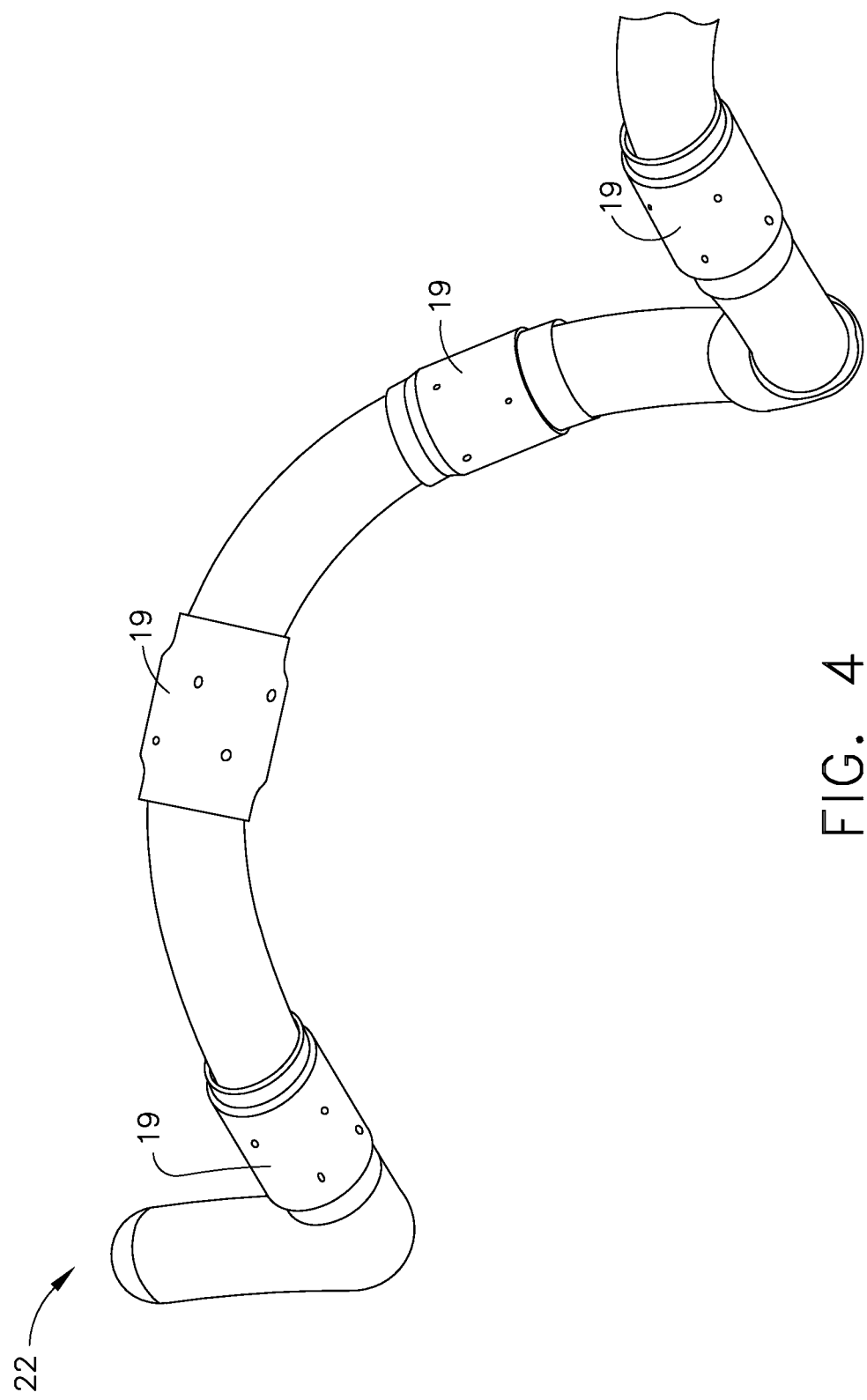

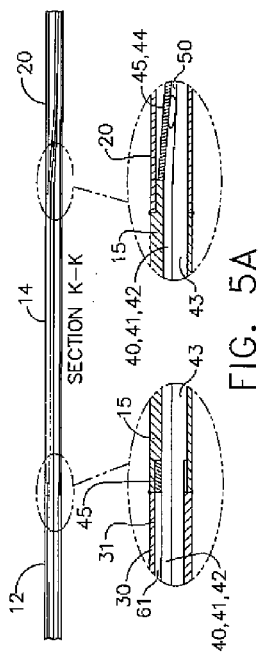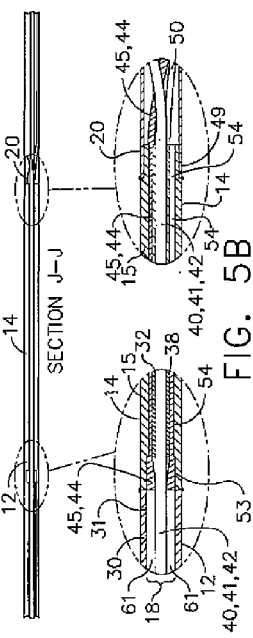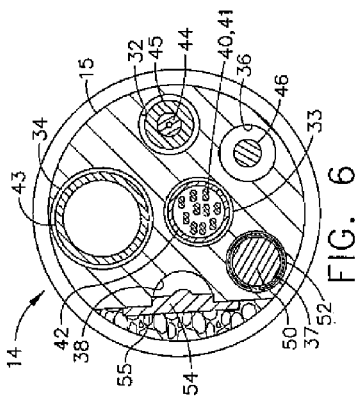

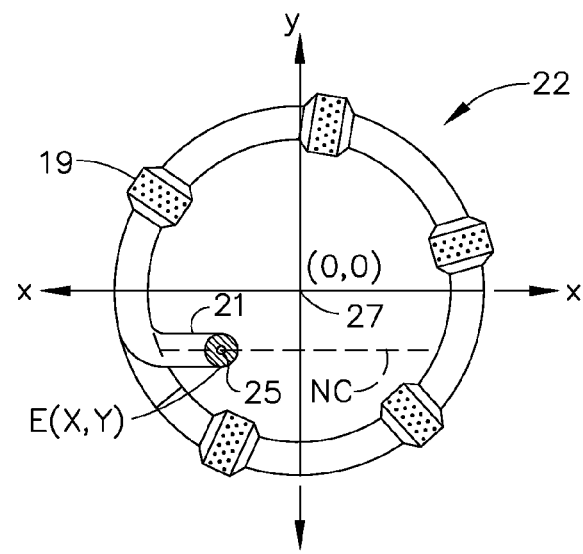
FIG. 8C
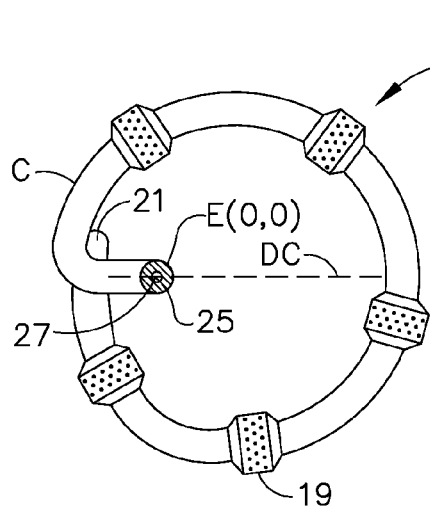 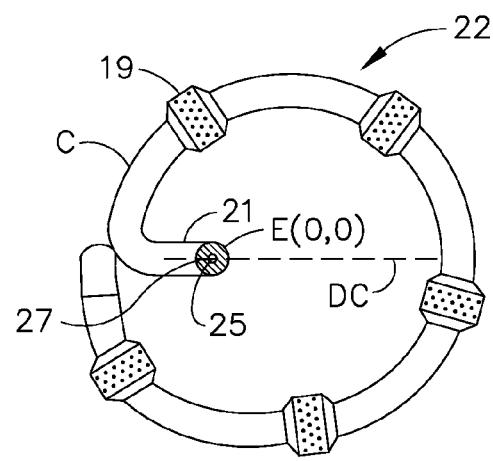
FIG. 8A  FIG. 8B

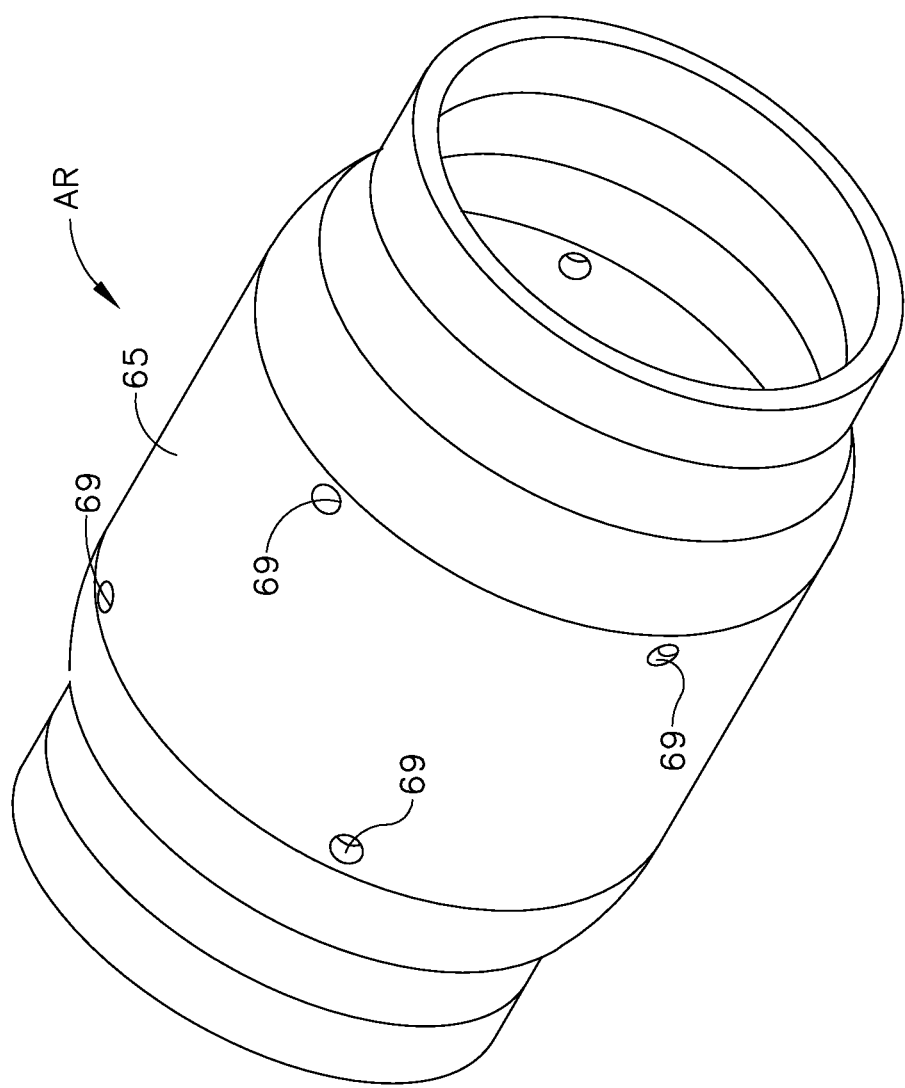

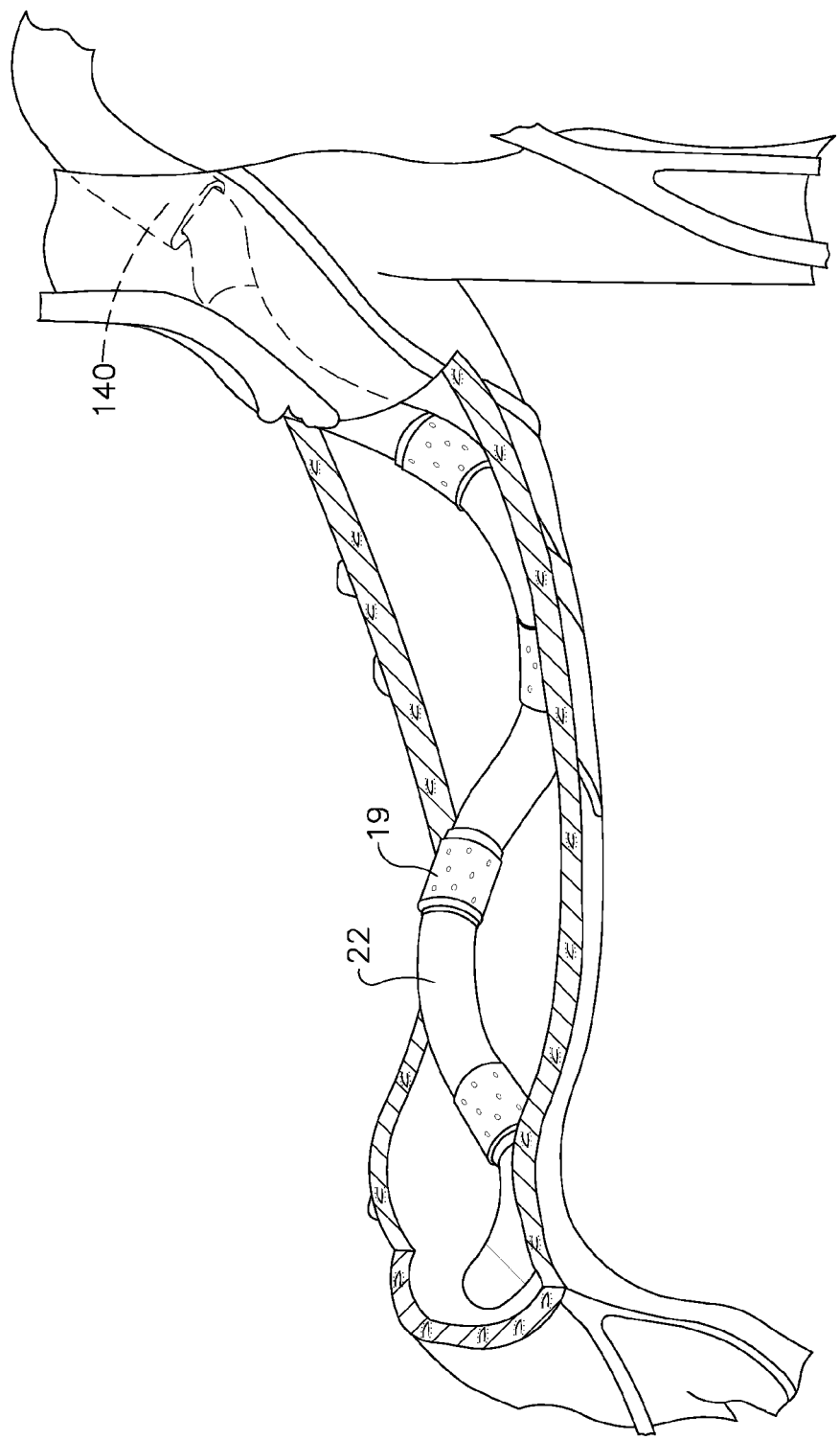

CATHETER WITH HELICAL END SECTION FOR VESSEL ABLATION

CROSS-REFERENCE TO RELATED APPLICATION

This application claims the benefit of U.S. Provisional Patent Application 61/646,688, filed May 14, 2012, which is incorporated herein by reference.

FIELD OF INVENTION

This invention relates generally to methods and devices for invasive medical treatment, and specifically to catheters, in particular, catheters having distal sections adapted for mapping and/or ablating selected vessel anatomy. More specifically, this invention relates to a catheter for ablating nerves and other tissue in a vessel such as a renal artery, pulmonary vein or other tubular vessel.

BACKGROUND

Ablation of myocardial tissue is well known as a treatment for cardiac arrhythmias. In radio-frequency (RF) ablation, for example a catheter is inserted into the heart and brought into contact with tissue at a target location. RF energy is then applied through an electrode on the catheter in order to create a lesion for the purpose of breaking current conduction paths in the tissue.

Additionally, the use of renal neurostimulation for the treatment of heart arrhythmias was disclosed in U.S. Patent Publication No. 2007/1029671 by Demaris et al. Demaris sets forth the use of neuromodulation to effectuate irreversible electroporation or electrofusion, ablation, necrosis and/or inducement of apoptosis, alteration of gene expression, action potential attenuation or blockade, changes in cytokine up-regulation and other conditions in target neural fibers. In some embodiments, such neuromodulation is achieved through application of neuromodulatory agents, thermal energy, or high intensity focused ultrasound.

In U.S. Patent Publication No. 2010/0222851 by Deem et al. the monitoring of renal neuromodulation was proposed stimulation to identify renal nerves to denervate or modulate. Stimulation of such nerves prior to neural modulation would be expected to reduce blood flow while stimulation after neural modulation would not be expected to reduce blood flow to the same degree when utilizing similar situation parameters and locations prior to neural modulation.

Recently, circumferential ablation of the pulmonary vein has gained acceptance as a treatment for atrial arrhythmias, and particularly for atrial fibrillation. For example, U.S. Pat. No. 6,064,902, whose disclosure is incorporated herein by reference, describes a catheter for ablating tissue on the inner wall of a blood vessel, such as a pulmonary vein. The tip portion of the catheter is deflectable from a first, generally straight, configuration, in which the proximal and distal sections are substantially co-linear, to a second, J-shaped, configuration in which the proximal and distal sections are generally parallel with a separation therebetween substantially corresponding to the inside diameter of the blood vessel. The distal end portion of the catheter is rotated about the longitudinal axis of the catheter to cause a circumferential displacement of proximal and distal ablation electrodes on the catheter along the inner wall of the pulmonary vein. In this way, the electrode catheter may be used to ablate a number of circumferentially-spaced sites on the inner wall of the pulmonary vein by ablating one or two sites at each circumferential position.

U.S. Patent Application Publication 2005/0033135, whose disclosure is incorporated herein by reference, describes a lasso for pulmonary vein mapping and ablation. A catheter for circumferentially mapping a pulmonary vein (PV) includes a curved section shaped to generally conform to the shape of the interior surface of the PV. The curved section is connected to catheter by a generally straight axial base section that is in an "on edge" configuration where the base axial section connects to the curved section on the circumference of the curved section. The curved section comprises one or more sensing electrodes, and its proximal end is joined at a fixed or generally known angle to a base section of the catheter. Position sensors are fixed to the curved section of the catheter and to the distal end of the base section. The catheter is inserted into the heart, and the curved section is positioned in contact with the wall of the PV, while the base section remains within the left atrium, typically positioned such that the joint with the curved section is at the ostium of the vein. The information generated by the three position sensors is used to calculate the locations and orientations of the sensing electrodes, which enables mapping of the surface of the PV. The sensing electrodes may additionally perform ablation of selected sites, or the catheter may further comprise ablation elements.

U.S. patent application Ser. No. 12/345,720, which is assigned to the assignee of the present patent application and whose disclosure is incorporated herein by reference, describes an alternative design in which the lasso is thicker and stiffer. Even so, operators can find lasso catheters to be difficult to maneuver within the heart and position in such a way that the entire circumference of the lasso is in contact with the tissue, as is desirable for effective pulmonary vein isolation.

U.S. patent application Ser. No. 13/174,742, which is assigned to the assignee of the present application and whose disclosure is incorporated herein by reference, describes a design which is adapted for use at the ostia or wall outside the vessel.

However, because human anatomy varies between individuals, the shape and size of a vessel such as a renal artery or a pulmonary vein vary, and the end section whether having an arcuate shape or a generally helical shape may not always fit the particular target ostium. Because of these factors, contact between the electrodes and the vessel wall is often less than complete and an ablation which effectively blocks conduction through the nerves in the vessel wall may not be complete. Accordingly, a desire exists for a catheter for ablation in a vessel which has a helical design so as to enable such an ablation in a vessel such as a renal artery or pulmonary vein.

SUMMARY OF THE INVENTION

The present invention is directed to a catheter whose distal assembly has a helical shape whose configuration that can either be static in diameter once deployed from a sheath or which in some embodiments be varied by means of a contraction wire actuated by a control handle and/or the use of a mandrel that is inserted into the distal assembly. For improved surface contact between the electrodes and the target tissue, e.g., a pulmonary vein or renal artery, the distal assembly includes a radially transverse section that supports the electrode-bearing curved portion of the distal assembly.

The configuration of the electrode-bearing portion of the distal assembly is generally curved or circular, including a helical form or a crescent shape, for mapping and/or ablating tubular regions, such as a pulmonary vein. The helical form may be tapered, either expanding in radius or decreasing in radius along its spiral or have a generally consistent diameter along its length. A support member with shape memory provides the desired configuration in the distal assembly and its flexibility can vary along its length. For example, the helical form may be stiffer in the proximal portion for withstanding load and more flexible in the distal portion for easier contraction. Such variable stiffness can be accomplished by varying the thickness of the support member, such as having a thicker proximal portion and a thinner distal portion.

To minimize the risk of charring, ablation ring electrodes carried on the distal assembly are irrigated. The ablation ring electrode has an enlarged mid-section so as to provide an annular gap or reservoir around the tubing carrying the ring electrode so that flow distribution to outside the electrode through apertures in the side wall of the ablation ring electrode is improved. Apertures are also provided in opposing end portions of the ring electrodes so that irrigation flows in the radial direction, as well as in the axial direction.

In a variable diameter configuration, a contraction wire can be actuated via the control handle to contract the distal assembly or a mandrel can be inserted through the distal assembly, or in particular, through the support member, to vary or alter the form of the electrode-bearing curved portion of the distal assembly. To facilitate this adjustment or variation, the support member can be hollow so as to receive the mandrel therethrough. To increase flexibility of the support member so that it can yield to the predetermined form of the mandrel while maintaining sufficient rigidness so that it can return its own predetermined form in the absence or withdrawal of the mandrel, the support member may be formed from a bundle of wires coiled in a spiral, or it may be a tubular member with a spiral cut along its length. The spiral cut may be smooth, or it may have an interlocking pattern such that the support member provides the desired flexibility without elongation in the axial direction.

The electrode-bearing portion of the distal assembly may include smaller and/or more closely spaced-together ring electrodes for impedance and/or PV potential recording. Accordingly, a single catheter can perform simultaneous ablation, mapping (electrogram recording) and assessment of tissue contact.

In one embodiment, the catheter includes an elongated body and a distal assembly with a shape-memory member defining a generally helical form. The catheter further includes a control handle adapted to actuate a deflection puller wire for deflecting a portion of the elongated body, and a contraction wire for contracting the generally helical form. The generally helical form which carries at least one ring electrode has an off-edge configuration relative to the elongated body such that a longitudinal axis of the elongated body does not intersect the circumference of the helical form and the generally helical form spirals about the longitudinal axis of the elongated body. Moreover, the helical form can have an on-axis configuration such that the longitudinal axis of the elongated body is axially aligned with a central longitudinal axis of the helical form, or an off-axis configuration such that these axes are axially offset from each other.

In a more detailed embodiment, the catheter has a distal assembly with a helical form carrying a plurality of irrigated ablation ring electrodes and a plurality of smaller ring electrodes adapted for impedance recording or PV potential recording. A control handle has a first control member that draws a contraction wire for contracting the helical form, and a second control member that draws a deflection wire for deflecting an intermediate section proximal of the distal assembly. A support member with shape memory extends through the distal assembly to provide the helical form. The support member has a varying stiffness along its length, for example, a decreasing stiffness toward a distal end of the support member.

In another more detailed embodiment, the support member is hollow so that it can receive a mandrel whose stiffness is greater than that of the support member so that the support member can yield to and generally assume the predetermined form of the mandrel. The support member may be of a hollow strand tube construction, or it may be a tubular construction with a spiral cut with either a smooth pattern or an interlocking pattern.

In a further embodiment, the helical section has a diameter which is sized so as to provide sufficient apposition to the walls of the lumen without requiring a contraction wire to vary its size. This embodiment provides a lower cost, easy to manufacture alternative to the contractible assembly. The control handle in the embodiment provides a means to manipulate the catheter and to house a connector and electrical connections as well as an irrigation luer and lumen to provide irrigation fluid to the distal end.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 4 is a perspective view of a distal assembly of a catheter in accordance with the present invention.

FIG. 5A is a side cross-sectional view of the catheter of FIG. 1, taken along line J-J.

FIG. 5B is a side cross-sectional view of the catheter of FIG. 1, taken along line K-K.

FIG. 6 is an end cross-sectional view of the catheter of FIG. 1, taken along line H-H.

FIG. 8A is an end view of a first embodiment of a distal assembly, with an off-edge, on axis configuration.

FIG. 8B is an end view of a second embodiment of a distal assembly, with an off-edge, on axis configuration.

FIG. 8C is an end view of a third embodiment of a distal assembly, with an off-edge, off axis configuration.

FIG. 11 is a perspective view of an embodiment of an irrigated ablation electrode.

FIGS. 20 and 21 are pictorial representation of the renal anatomy showing insertion of the catheter into the renal artery.

DETAILED DESCRIPTION OF THE INVENTION

Figure 1:
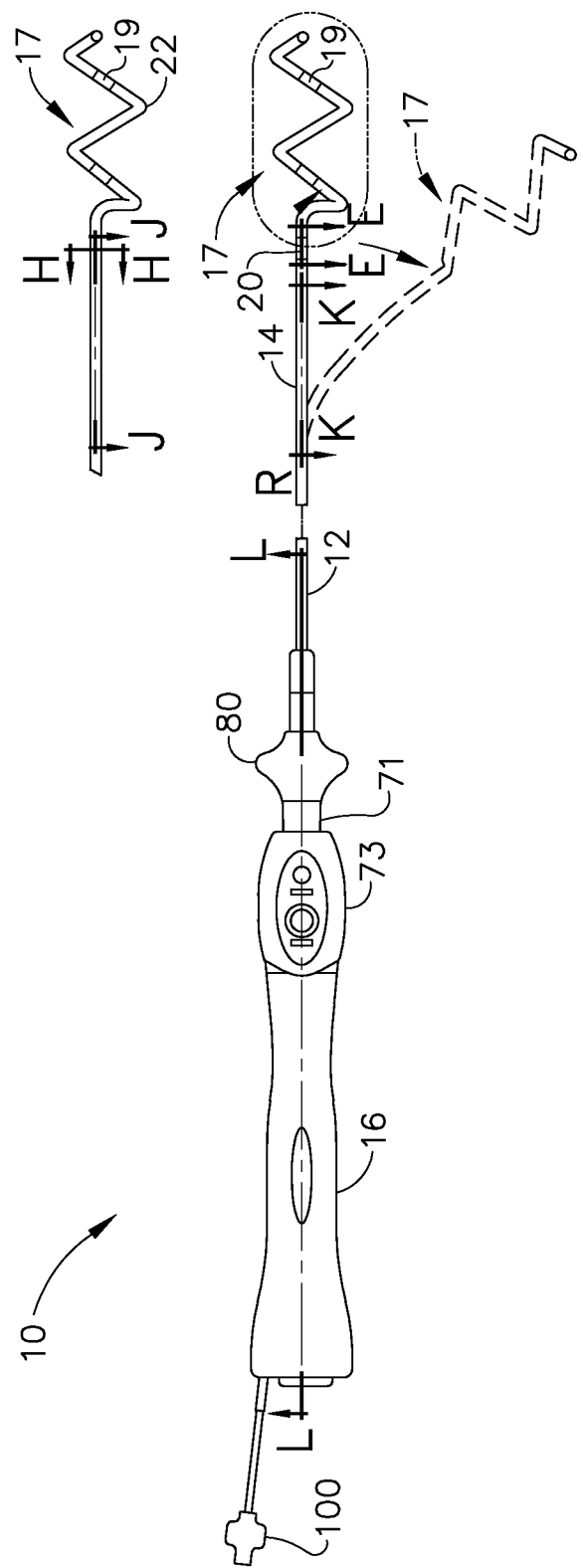
FIG. 1 is a top plan view of an embodiment of a catheter in accordance with the present invention.

Referring to FIGS. 1-4, a catheter 10 according to the disclosed embodiments comprises an elongated body that may include an insertion shaft/catheter body 12 having a longitudinal axis, and an intermediate section 14 distal of the catheter body that can be uni- or bi-directionally deflected off axis from the catheter body longitudinal axis. A resilient three-dimensional distal assembly 17, with ring electrodes 19 disposed along a nonlinear or curved distal portion, extends from a generally straight transitional section 20 distal of the elongated body or the intermediate section 14. In accordance with a feature of the present invention, the curved distal portion defines, when unconstrained, a generally helical form 22. The helical form is oriented obliquely relative to a longitudinal axis of the intermediate section 14. The term "obliquely", in the context of the present invention means that the plane in space that best fits the helical form is angled relative to the longitudinal axis of the intermediate section 14. The angle between the plane and the axis ranges between about 30 degrees to approximately 60 degrees, preferably about 45 degrees. Moreover, the helical form spirals or subtends in a predetermined manner. In one embodiment, the helical form subtends significantly greater than 360 degrees, preferably more than 520 degrees and most preferably approximately 540 degrees.

Figure 2:
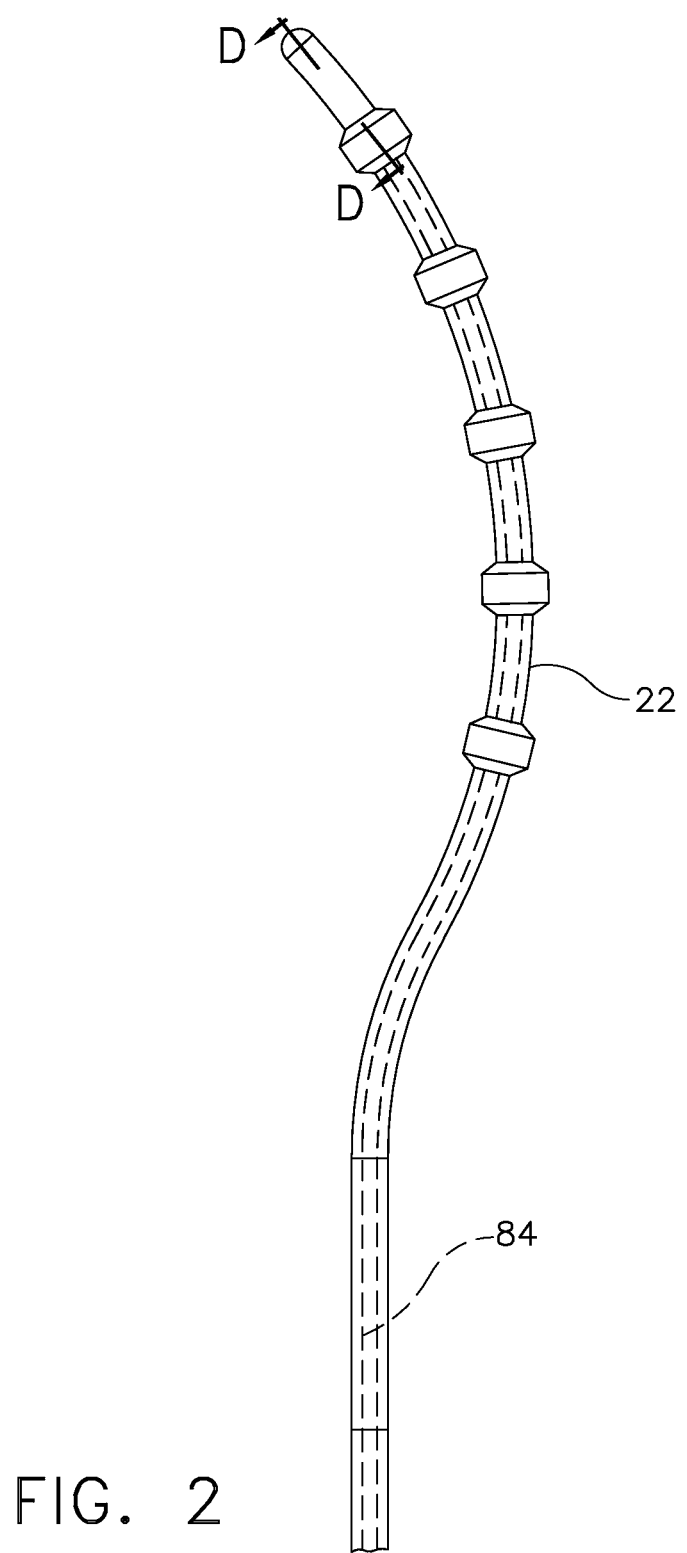
FIG. 2 is a side view of an embodiment of a distal end portion of a catheter of the present invention, including a distal assembly.

In one embodiment of catheter 10 is designed to allow the helical form 22 to be contracted and expanded, thus decreasing its radius and/or pitch, by an operator manipulating controller 73 in a control handle 16 at the proximal end of the catheter body 12, as explained below in further detail. Furthermore, as illustrated in FIG. 2, the present catheter allows the overall configuration of the helical form 22 to be varied and adjusted, including significant expansion, whereby the helical form can be generally straightened, by means of a mandrel member 84 that is inserted alongside with or through a shape-memory member 50 that provides the helical form 22 of the distal assembly 17, as also explained below in further detail. In another embodiment of catheter 10 the contraction mechanism is not in place and the concomitant puller wires and mechanisms to contract the helical distal end are removed providing a distal assembly that takes one pre-determined shape upon exiting from the guiding sheath and/or having an internal mandrel 84 removed. This embodiment is discussed in more detail below. If a mandrel 84 is used it may be removed only from the tip section or from the catheter entirely. Once the mandel is removed the tip section expands to the helical form 22 by the shape-memory material of which it is formed.

Alternatively, rather than using an internal mandrel 84, a guidewire may be used for a similar purpose. The guidewire is introduced first into the renal artery or pulmonary vein. Catheter 10 is then advanced over the guidewire. Once the tip section is in the proper location the guidewire can be removed and the distal assembly 17 will expand to take the helical form 22 dictated by the internal shape memory material.

The catheter enters a patient's body through a guiding sheath that has been inserted in a body cavity, such as a heart chamber, abdominal aorta or renal artery. Due to the flexible construction of the distal assembly 17, the helical form 22 readily straightens for insertion into the guiding sheath. The distal assembly is advanced axially in the guiding sheath until it moves past the distal end of the guiding sheath toward the interior of the vessel to be ablated such as the pulmonary vein or the renal artery. (The term "axial" refers to the direction parallel to the longitudinal axis of the catheter). When exposed and unconstrained, the distal assembly 17 reassumes the helical form 22 which is maneuvered to engage the tissue with some or all of the electrodes 19 on the helical form contacting the tissue surface of the tubular anatomical structure simultaneously, as shown and described hereinbelow with respect to FIGS. 19-21.

According to an embodiment of the present invention, the catheter 10 has a three-dimensional mapping and/or ablation assembly 17 at its distal end. As shown in FIG. 1, the catheter comprises an elongated insertion shaft/catheter body 12 having proximal and distal ends, a deflectable intermediate section 14, a control handle 16 at the proximal end of the catheter body, and a distal assembly 17 mounted at the distal end of the deflectable intermediate section.

In the depicted embodiment of FIGS. 1 and 5A, 5B, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 30 made of polyurethane or PEBAX. The outer wall 30 comprises an imbedded braided mesh of stainless steel or the like, as is generally known in the art, to increase torsional stiffness of the catheter body 12 so that, when the control handle 16 is rotated, the intermediate section 14 and distal assembly 17 will rotate in a corresponding manner.

The outer diameter of the catheter body 12 is not critical, but is preferably no more than about 8 french, more preferably approximately 5 french. Likewise the thickness of the outer wall 30 is not critical, but is thin enough so that the central lumen 18 can accommodate any desired wires, cables and/or tubes. The inner surface of the outer wall 30 is lined with a stiffening tube 31 to provide improved torsional stability. The outer diameter of the stiffening tube 31 is about the same as or slightly smaller than the inner diameter of the outer wall 30. The stiffening tube 31 can be made of any suitable material, such as polyimide, which provides very good stiffness and does not soften at body temperature.

The deflectable intermediate section 14 comprises a short section of tubing 15 having multiple lumens, each occupied by the various components extending through the intermediate section. In the illustrated embodiment of FIG. 6, there are six lumens. Lead wire/thermocouple pairs 40, 41 for each ring electrode pass through a first lumen 33. A nonconductive protective sheath 42 may be provided. Irrigation tubing 43 for delivering irrigation fluid to the distal assembly 17 passes through a second lumen 34. A contraction wire 44 passes through a third lumen 32 in a variable diameter/contractible design. A cable 46 for a position sensor assembly 48, including a plurality of single axis sensors (SAS) positioned on the distal assembly 17, passes through a fourth lumen 36. For the distal assembly 17, a shape-memory support member 50 surrounded by a nonconductive tubing 52, e.g., a polyimide tubing, extends proximally from the distal assembly 17 for a relatively short distance into a fifth lumen 37. A puller wire 54 for deflecting the intermediate section 14 passes through a sixth lumen 38.

The multi-lumened tubing 15 of the intermediate section 14 is made of a suitable non-toxic material that is preferably more flexible than the catheter body 12. A suitable material is braided polyurethane or PEBAX, i.e., polyurethane or PEBAX with an embedded mesh of braided stainless steel or the like. The plurality and size of each lumen are not critical, provided there is sufficient room to house the components extending therethrough. Position of each lumen is also not critical, except the position of the third lumen 32 for the distal assembly contraction wire 44 is preferably more aligned with an inner circumference of the helical form 22 of the distal assembly 17 so that proximal movement of the wire can readily contract the helical form. Moreover, the sixth lumen 38 for the deflection wire 54 is off-axis so that distal movement of the deflection wire accomplishes deflection toward the side on which lumen is off axis. Preferably, the third and sixth lumens 32 and 38 are diametrically opposed to each other.

The useful length of the catheter, i.e., that portion that can be inserted into the body excluding the distal assembly 17, can vary as desired. Preferably the useful length ranges from about 110 cm to about 120 cm for a catheter to be used in the pulmonary vein through an access point in the femoral artery and 80 cm to about 100 cm for a catheter to be used in the renal anatomy through the same access point. The length of the intermediate section 14 is a relatively small portion of the useful length, and preferably ranges from about 3.5 cm to about 10 cm, more preferably from about 5 cm to about 6.5 cm. If access to the anatomical structure of the renal arteries to be treated is through a radial artery the preferred length for treatment would be approximately 120 cm to about 150 cm.

A preferred means for attaching the catheter body 12 to the intermediate section 14 is illustrated in FIGS. 5A and 5B. The proximal end of the intermediate section 14 comprises an inner circumferential notch that receives the outer surface of the stiffening tube 31 of the catheter body 12. The intermediate section 14 and catheter body 12 are attached by glue or the like, for example, polyurethane. If desired, a spacer (not shown) can be provided within the catheter body 12 between the distal end of the stiffening tube 31 and the proximal end of the intermediate section 14 to provide a transition in flexibility at the junction of the catheter body 12 and the intermediate section, which allows the junction to bend smoothly without folding or kinking. An example of such a spacer is described in more detail in U.S. Pat. No. 5,964,757, the disclosure of which is incorporated herein by reference.

Figure 7:
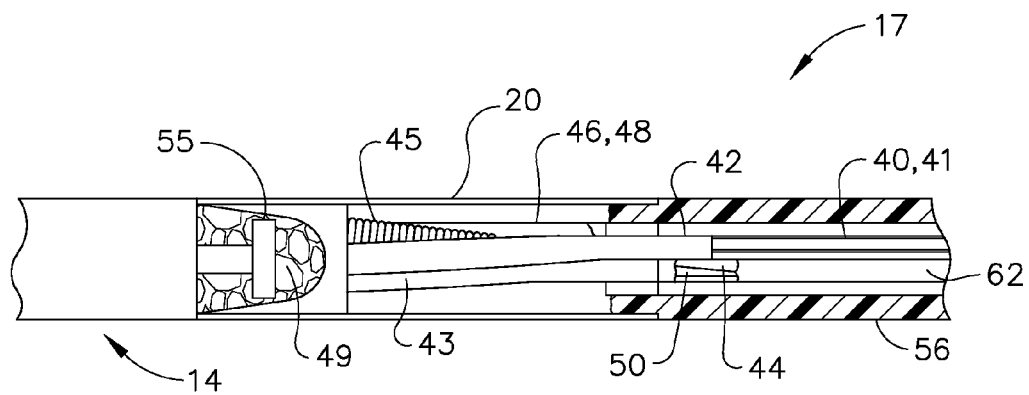
FIG. 7 is a side cross-sectional view of a section of the distal end portion of FIG. 1, as delineated by line E-E.

Distal the intermediate section 14 is the distal assembly 17. Extending between the intermediate section 14 and the distal assembly 17 is a transitional section 20, as shown in FIGS. 1 and 7, having a tubing of suitable material, e.g., PEEK, with a central lumen that allows the various components extending therethrough to reorient before entering the distal assembly 17.

Figure 3:
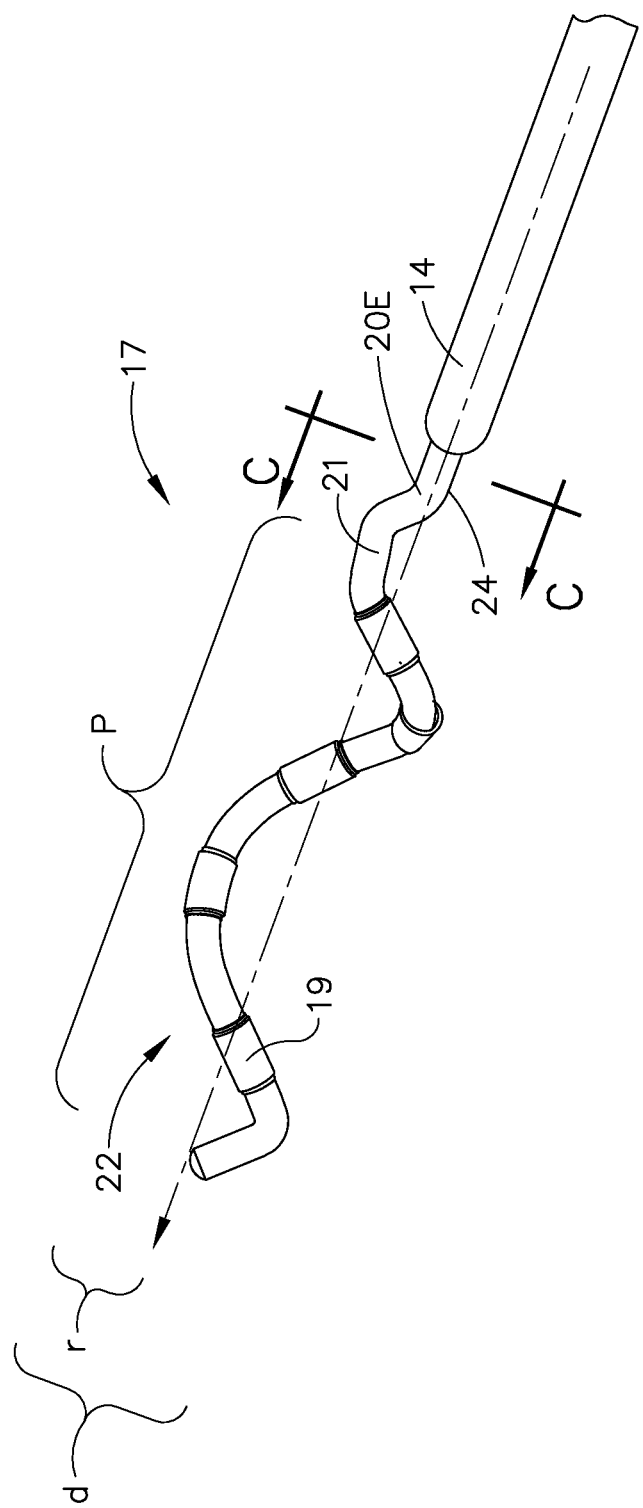
FIG. 3 is a perspective view of an embodiment of a distal assembly.

As shown in FIG. 3, at a base of the helical form 22, the distal assembly 17 includes a generally straight proximal section 24 and a generally straight transverse section 21. The distal end of the proximal portion 24 and the proximal end of the transverse portion form an "elbow" 20E at their junction such that the transverse portion 21 is generally transverse to the longitudinal axis 25 of the catheter 10 or at least the intermediate section 14. In accordance with a feature of the present invention, the helical form 22 is mounted on the catheter in an "off-edge" configuration, where longitudinal axis 25 of the intermediate section 14 does not intersect the circumference of the helical form 22 but rather extends through the interior of the helical form as shown in FIGS. 8A-8C.

In the embodiments of FIGS. 8A and 8B, center longitudinal axis 27 of the helical form 22 is generally aligned with the longitudinal axis 25 of the intermediate section, that is, the helical form 22 is axially centered ("on axis") on the longitudinal axis 25 of the intermediate section 14. In the embodiment of FIG. 8C, the respective longitudinal axes 25, 27 are parallel and offset or off alignment relative to each other such that the helical form 22 is "off axis" relative to the longitudinal axis 25. Where the interior of the helical form is defined by a centered X/Y Cartesian coordinate system, the elbow E generally assumes the central (0,0) position in an on-axis configuration, and an (x≠0, y≠0) position in an off-axis configuration. The transverse section 21 can have any length between about zero and the diameter of the helical form and can lie on any diametrical chord DC (FIGS. 8A and 8B) or nondiametrical chord NC (FIG. 8C).

With reference to FIG. 3, the helical form 22 can be defined by a radius r (or diameter d) and a pitch P (number of turns per unit length along its longitudinal axis). The diameter suitable for mapping and/or ablating a PV can range between about 15 mm and 30 mm. The pitch can range between about 1.0 cm and 2.0 cm (distance between periods of 360 degrees). The diameter suitable for mapping and/or ablating a renal artery is preferably between 4 and 10 mm with a pitch ranging between 0.5 cm and 1.0 cm. A catheter having a helical diameter of approximately 10 mm can fit inside a vessel larger than 4 mm while providing force sufficient to have the wall apposition necessary to create contact between electrodes 19 and the tissue.

In accordance with an additional feature of the present invention, the helical form 22 may be tapered along its length. In one embodiment, the helical form spirals outwardly with an increasing radius from its proximal end to its distal end (FIG. 8B). In another embodiment, the helical form spirals inwardly with a decreasing radius from its proximal end to its distal end (FIG. 8A). In yet another embodiment, the helical form has a generally constant radius along its length (FIG. 8C).

Depending on the arrangement of the transverse section 21, including variations on the (x, y) position of the elbow E, different contact properties may be achieved with the distal assembly 17 for use in different vessel anatomies where a vessel may vary in diameter along its length.

In the illustrated embodiment of FIG. 3, the helical form 22 extends distally from the transverse section 21 and generally spirals about a longitudinal axis of the proximal section 24. The helical form 22 has an outer diameter d preferably ranging to about 33 mm to about 35 mm. The helical form 22 can curve in a clockwise direction or a counterclockwise direction. The proximal section 24 of the distal assembly 17 has an exposed length of about 5 mm.

Figure 9:
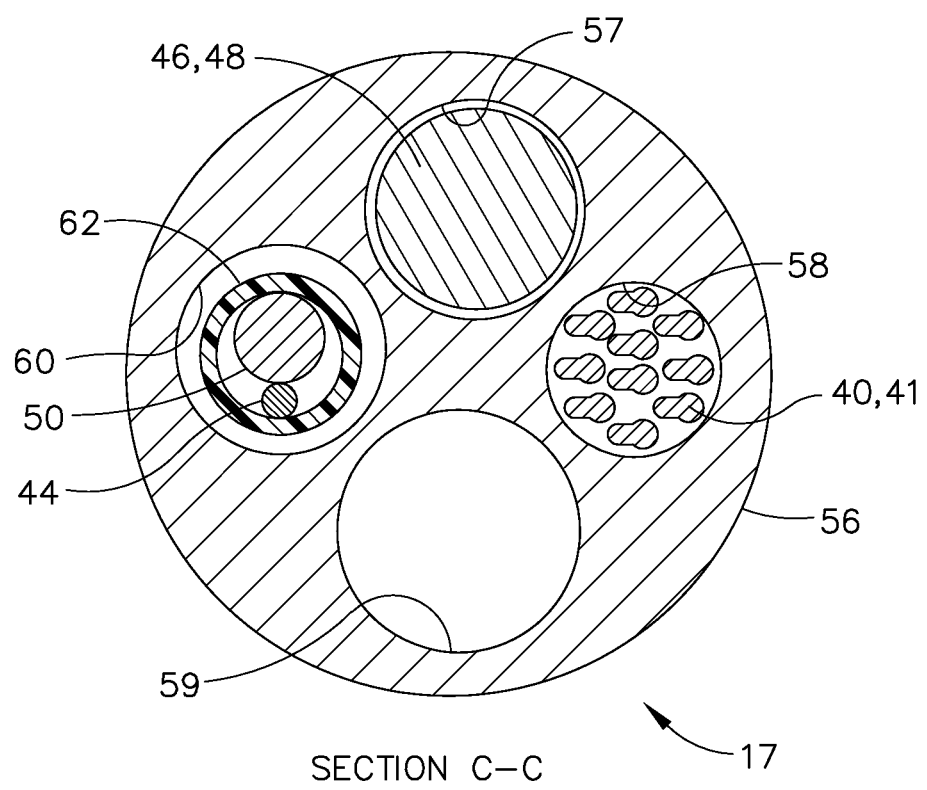
FIG. 9 is an end cross-sectional view of a section of the distal end portion of FIG. 3, taken along line C-C.

As shown in FIG. 9, the distal assembly 17 is formed of multi-lumened tubing 56 which can be preformed with a desirable shape, including the helical form, as understood by one of ordinary skill in the art. In the disclosed embodiment, the tubing 56 has four off-axis lumens, namely, a first lumen 57 for the cable 46 and optionally the SAS 48, a second lumen 58 for the ring electrode wire pairs 40, 41, a third lumen 59 for irrigation fluid, and a fourth lumen 60 for the support member 50 and the contraction wire 44. Again, position and sizing of the lumens is not critical, except the position of the fourth lumen 60 for the contraction wire 44 is preferably on an inner circumference of the helical form so that proximal movement of the wire can readily contract the helical form. The tubing 56 can be made of any suitable material, and is preferably made of a biocompatible plastic such as polyurethane or PEBAX.

In the depicted embodiment, the pre-formed support or spine member 50 of the distal assembly 17 extends through the fourth lumen 60 of the tubing 56 to define the shape of the helical form 22. The support member 50 is made of a material having shape-memory, i.e., that can be straightened or bent out of its original shape upon exertion of a force and is capable of substantially returning to its original shape upon removal of the force. A particularly preferred material for the support member 50 is a nickel/titanium alloy. Such alloys typically comprise about 55% nickel and 45% titanium, but may comprise from about 54% to about 57% nickel with the balance being titanium. A preferred nickel/titanium alloy is Nitinol, which has excellent shape memory, together with ductility, strength, corrosion resistance, electrical resistivity and temperature stability.

The support member 50 has a cross-section of a predetermined shape that may be generally circular or generally rectangular, including a square shape. It is understood that a generally rectangular cross section can provide greater stiffness compared to a helical cross-section of a comparable size. Moreover, the support member can have a varying thickness along its length, for example, being thinner distally and thicker proximally so that a distal portion can be more readily contracted and a proximal portion can better withstand the load from an axial force that is applied when the distal assembly 17 comes into contact with target tissue.

In one embodiment, the support member 50 has a proximal end just proximal of the junction between the intermediate section 14 and the transitional section 21, for example, about 2-3 mm proximal of the junction in the fifth lumen 37. Alternatively, the support member 50 can extend further proximally into the intermediate section 14 via the fifth lumen or another lumen, the catheter body 12 via the central lumen 18, or further into the control handle 16, as desired or appropriate. In either instance, a nonconductive protective tubing 62 (e.g., a braided polyimide tubing) is provided in surrounding relationship with the support member 50 along its length.

The contraction wire 44 is provided to contract the helical form 22 to reduce its diameter. The contraction wire 44 has a proximal end anchored in the control handle 16, which is used to manipulate the contraction wire. The contraction wire 44 extends through the central lumen 18 of the catheter body 12, through the third lumen 32 of the intermediate section 14, the central lumen of the transitional section 20 and the fourth lumen 60 of the distal assembly 17 to its distal end. In the fourth lumen 60 of the distal assembly 17, the contraction wire 44 extends through the nonconductive protective tubing 62 along with the support member 50. As mentioned, the fourth lumen 60 of the distal assembly 17 is positioned on the side of the helical form 22 closer to its center. With this arrangement, contraction of the helical form 22 is dramatically improved over arrangements where the position of the contraction wire 44 is not so controlled.

In one embodiment, the nonconductive protective tubing 62 comprises three layers, including an inner layer of polyimide over which a braided layer is formed, the braided layer comprising a braided stainless steel mesh or the like, as is generally known in the art. The braided layer enhances the strength of the tubing, reducing the tendency for the contraction wire 44 to straighten the preformed curve of the distal assembly 17. A thin plastic layer of polytetrafluoroethylene is provided over the braided layer to protect the braided layer. The plastic tube 62 has a proximal end anchored to the distal end of the intermediate section 14.

Figure 10:
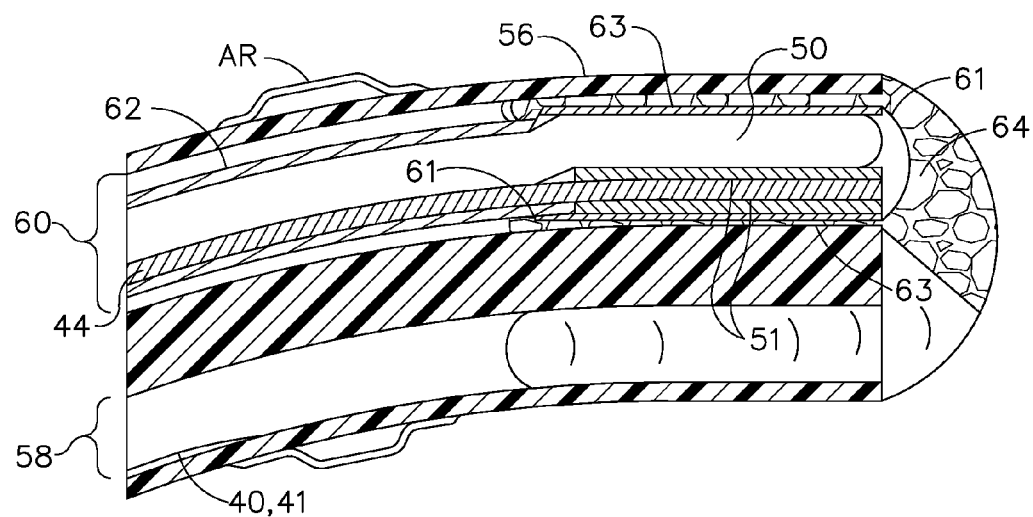
FIG. 10 is a side cross-section view of a distal tip of the distal end portion of FIG. 2, taken along line D-D.

The support member 50 extends through the protective tubing 62 along with the contraction wire 44. In the illustrated embodiment of FIG. 10, the distal ends of the support member 50 and the contraction wire 44 (anchored in a crimped ferrule 51) are soldered or otherwise attached to a small stainless steel tube 63. With this arrangement, the relative positions of the contraction wire 44 and the support member 50 can be controlled so that the contraction wire 44 can be positioned on the inner side of the helical form 22 closer to the center of the helical form, as described above. The contraction wire 44 on the inside of the curve pulls the support member 50 to the inside of the curve, enhancing contraction of the helical form. Further, when the protective tubing 62 includes a braided layer, it minimizes the risk of the contraction wire 44 tearing through the multi-lumen tubing 56 of the distal assembly 17. In the depicted embodiment, the distal end of the multi-lumen tubing 56 of the distal assembly 17 is sealed closed with a dome 64 of polyurethane glue or the like.

With reference to FIGS. 5A and 5B, the compression coil 45 surrounding the contraction wire 44 extends from the proximal end of the catheter body 12 and through the third lumen 32 of the intermediate section 14. The compression coil has a distal end at or near a mid-location in the transitional section 20. The compression coil 45 is made of any suitable metal, preferably stainless steel, and is tightly wound on itself to provide flexibility, i.e., bending, but to resist compression. The inner diameter of the compression coil is preferably slightly larger than the diameter of the contraction wire 44. The outer surface of the compression coil is covered by a flexible, non-conductive sheath 47, e.g., made of polyimide tubing. The compression coil preferably is formed of a wire having a square or rectangular cross-sectional area, which makes it less compressible than a compression coil formed from a wire having a helical cross-sectional area. As a result, the compression coil 45 keeps the catheter body 12, and particularly the intermediate section 14, from deflecting when the contraction wire 44 is manipulated to contract the distal assembly 17 as it absorbs more of the compression.

Figure 12:
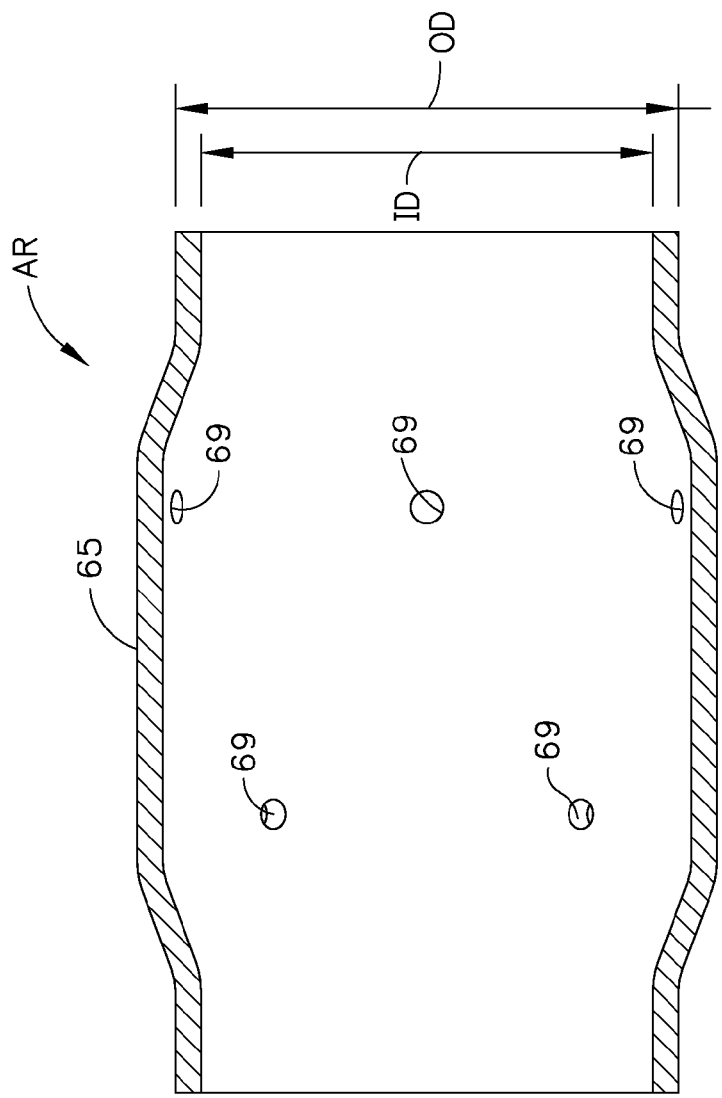
FIG. 12 is a cross-sectional view of the irrigated ablation electrode of FIG. 11
Figure 13:
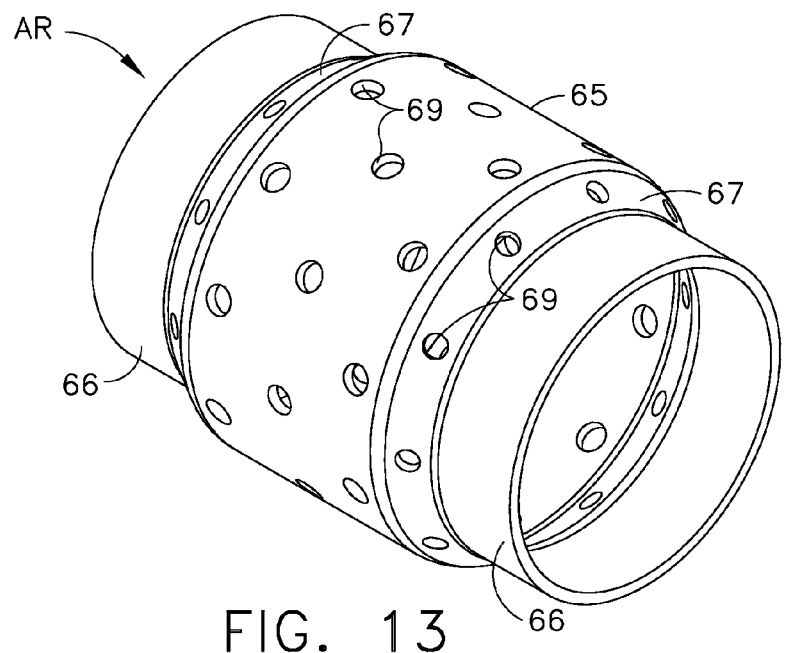
FIG. 13 is a perspective view of an embodiment of an irrigated ablation electrode.

A series of ring electrodes 19 are mounted on predetermined locations on the helical form 22, as shown in FIGS. 1, 3 and 4. The electrodes can be made of any suitable solid conductive material, such as platinum or gold, preferably a combination of platinum and iridium or gold and platinum, and mounted onto the tubing with glue or the like. Suitable embodiments of electrodes adapted for ablation and irrigation are illustrated in FIGS. 11-13. The ablation reservoir ("AR") electrode is generally cylindrical with a length greater than its diameter. In one embodiment in FIGS. 11 and 12, the length is about 1 to 4 mm, in length the outer diameter (OD) is about 2.5 mm and the inner diameter (ID) is about 2.23 mm and the number of which embodiment is optimized for use in the renal anatomy. In another embodiment in FIG. 13, the length is about 3.0 mm, the outer diameter is about 2.8 mm, and the inner diameter is about 2.33 mm.

Figure 14:
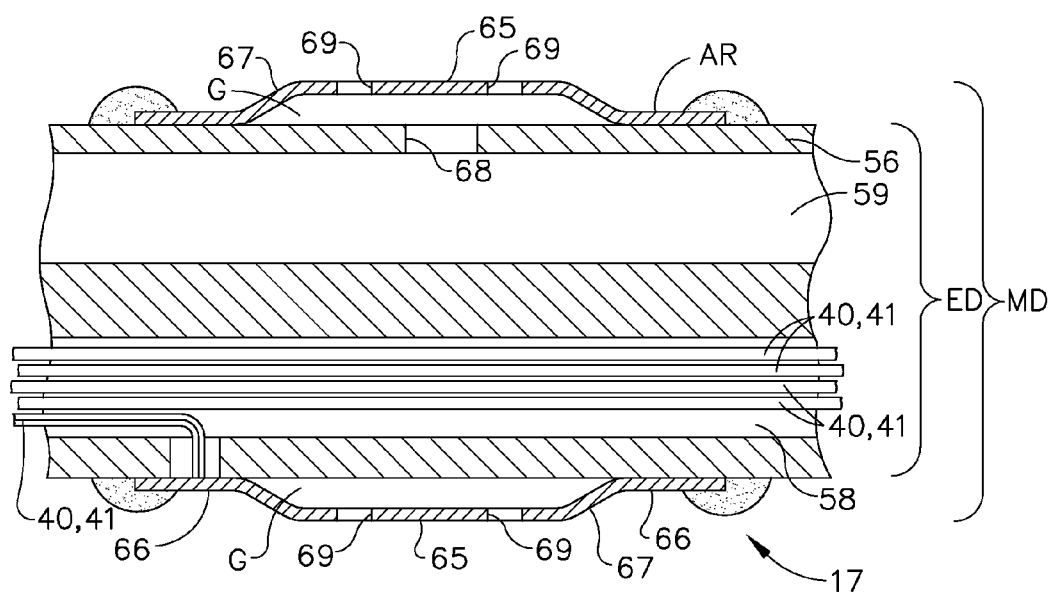
FIG. 14 is a side cross-sectional view of a portion of an embodiment of a distal assembly carrying an irrigated ablation electrode.

In the illustrated embodiments further depicted in cross-section in FIG. 14, the AR electrode has a side cross-section that can resemble a barrel with a side wall 65 (with a width, in one embodiment, of about 2.5 mm) that bulges radially such that a mid portion diameter MD is greater than end diameter ED at opposing end portions 66. Curved transitional regions 67 are provided between the side wall 65 and the end portions 66 to provide an atraumatic profile without corners or sharp edges.

Notably, the mid portion diameter is greater than the outer diameter of the underlying tubing 56 of the distal assembly so that a reservoir or annular gap G exists around the exterior of the tubing 56. The gap G provides improved fluid distribution from the third lumen 59 to the exterior of the AR electrode via an opening 68 provided in the outer wall of the tubing 56 and apertures 69 strategically formed and positioned in the side wall 65 of the AR electrode. The size of the opening 68 in the tubing 56 varies with the position along the length of the helical form 22. For optimum flow, the more distal an opening is along the helical form, the greater the size or cross-section of the opening and/or the plurality of openings for each AR electrode.

The apertures 69 are arranged the side wall 65 of an AR electrode in a predetermined pattern including axially offset rows. These apertures face outwardly promoting flow in a radial direction. Apertures are also provided in or near the curved transitional regions 67 to promote flow in an axial direction. Moreover, these apertures are particularly effective in minimizing charring and coagulation at or near the curved transitional regions which are likely to be "hot spots" resulting from higher current densities due to transitions in the electrode profile. In that regard, the plurality and/or cross-section of the apertures is greater at or near the curved transitional regions than in the side wall of the electrode so as to provide more cooling in the curved transitional regions. As such, the catheter can deliver more irrigation and consequently more cooling without increasing overall flow rate and overall fluid load on the patient.

In one embodiment, in FIGS. 11 and 12 there are there are about 10 apertures on side wall 65 and no other apertures. In the embodiment in FIG. 13 there are about 10 apertures on each of the curved transitional regions 67 and 20 on side wall 65. The pattern may be adjusted to further modify the flow distribution from each AR electrode. The pattern can be adjusted by adding or removing apertures, modifying the spacing between the apertures, modifying the location of the apertures on the ring electrodes and/or modifying the aperture geometry. Other suitable ring electrodes are described in US Patent Application Publication No. US2010/0168548 A1, the entire content of which is hereby incorporated by reference.

Irrigation fluid is delivered to the distal assembly by the irrigation tubing 43 whose proximal end is attached to a luer hub 100 proximal of the control handle 16 and receives fluid delivered by a pump (not shown). The irrigation tubing extends through the control handle 16, the central lumen 18 of the catheter body 12, the second lumen 34 of the intermediate section 14, the central lumen of the transitional section 20 and a short distance distally into the third lumen 59 of the distal assembly 17, for example, about 5 mm. The fluid enters the third lumen 59 where it exits the lumen via the openings 68 into the reservoir R of the AR electrodes where it exits the reservoir via the apertures 69 to outside of the AR electrodes to minimize charring.

The number of AR electrodes on the distal assembly 17 can vary as desired. Preferably the number of AR electrodes ranges from about 3 to about 12, more preferably from about 5 to 7. In one embodiment, the distal assembly 17 carries ten AR electrodes. The electrodes can be approximately evenly spaced around the helical form 22, as shown in FIG. 3.

The proximal end of each wire 50 is electrically connected to a suitable connector (not shown) distal of the control handle 16 for transmitting and/or receiving electrical signals to accomplish ablation. Each AR electrode is connected to a respective pair of wires 40, 41. In the disclosed embodiment, wire 40 of the wire pair is a copper wire, e.g. a number "40" copper wire. The other wire 41 of the wire pair is a constantan wire. The wires of each pair are electrically isolated from each other except at their distal ends where they are twisted together, fed through a hole formed in the second lumen 58 of the distal assembly 17, and soldered to their respective AR electrode (FIG. 14). The wire pairs for each electrode extend from the control handle 16, through the central lumen 18 of the catheter body 12, the first lumen 33 of the intermediate section 14, the central lumen of the transitional section 20, and the second lumen 58 of the distal assembly 17. Ablation energy, e.g., RF energy, is delivered to the AR electrodes via the wire 40 of the wire pairs. However, the wire pairs inclusive of their respective constantan wire can also function as temperature sensors or thermocouples sensing temperature of each AR electrode.

All of the wire pairs pass through one nonconductive protective sheath 42 (FIG. 6), which can be made of any suitable material, e.g., polyimide, in surrounding relationship therewith. The sheath 42 extends from the control handle 16, the catheter body 12, the intermediate section 14, the transitional section 20 and into the second lumen 58 of the distal assembly 17, terminating just distal of the junction between the transitional section 20 and the distal assembly 17, for example, about 5 mm into the second lumen 58. The distal end is anchored in the second lumen by glue, for example, polyurethane glue or the like.

In a deflectable version of the catheter, a deflection puller wire 54 is provided for deflection of the intermediate section 14. The deflection wire 54 extends through the central lumen 18 of the catheter body 12 and the sixth lumen 38 of the intermediate section 14. It is anchored at its proximal end in the control handle 16, and at its distal end to a location at or near the distal end of the intermediate section 14 by means of a T-bar 55 (FIG. 7) that is affixed to the sidewall of the tubing 32 by suitable material 49, e.g., polyurethane. The distal end is anchored to the sidewall of the tubing 15 of the intermediate section as is generally described in U.S. Pat. No. 6,371,955, the entire disclosure of which is incorporated herein by reference. The puller wire 54 is made of any suitable metal, such as stainless steel or Nitinol, and is preferably coated with Teflon® or the like. The coating imparts lubricity to the puller wire. The puller wire preferably has a diameter ranging from about 0.006 to about 0.010 inch.

A second compression coil 53 is situated within the central lumen 18 of the catheter body 12 in surrounding relation to the puller wire 54 (FIGS. 5A and 5B). The second compression coil 53 extends from the proximal end of the catheter body 12 to at or near the proximal end of the intermediate section 14. The second compression coil 53 is made of any suitable metal, preferably stainless steel, and is tightly wound on itself to provide flexibility, i.e., bending, but to resist compression. The inner diameter of the second compression coil 53 is preferably slightly larger than the diameter of the puller wire 54. The Teflon® coating on the puller wire allows it to slide freely within the second compression coil. Within the catheter body 12, the outer surface of the second compression coil 53 is covered by a flexible, non-conductive sheath 61, e.g., made of polyimide tubing. The second compression coil 53 is anchored at its proximal end to the outer wall 30 of the catheter body 12 by a proximal glue joint and to the intermediate section 14 by a distal glue joint.

Within the sixth lumen 38 of the intermediate section 14, the puller wire 54 extends through a plastic, preferably Teflon®, puller wire sheath, which prevents the puller wire 54 from cutting into the wall of the tubing 15 of the intermediate section 14 when the intermediate section 14 is deflected.

Longitudinal movement of the contraction wire 44 relative to the catheter body 12, which results in contraction of the helical form of the distal assembly 17, is accomplished by suitable manipulation of the control handle 16. Similarly, longitudinal movement of the deflection wire 54 relative to the catheter body 12, which results in deflection of the intermediate section 14, is accomplished by suitable manipulation of the control handle 16. Suitable control handles for manipulating more than one wire are described, for example, in U.S. Pat. Nos. 6,468,260, 6,500,167, and 6,522,933, the disclosures of which are incorporated herein by reference. Suitable control handles for manipulating lasso-type catheters are described in U.S. application Ser. No. 12/550,307, filed Aug. 28, 2009, and U.S. application Ser. No. 12/550,204, filed Aug. 28, 2009, the entire disclosures of which are incorporated herein by reference.

Alternatively, a catheter having the distal assembly of the present invention could be made in accordance with FIG. 22 discussed later where there is no deflection or helical contraction/expansion mechanisms. The helical design with shape memory element provides the force necessary for contact of the catheter to the artery wall, eliminating the need for component manipulation (deflection and contraction/expansion). For the catheters that do not need any deflection or contraction/expansion means, a simple handle with a connector and an irrigation port is all that is necessary. This embodiment is shown and described with respect to FIG. 24 A et seq.

Figure 15:
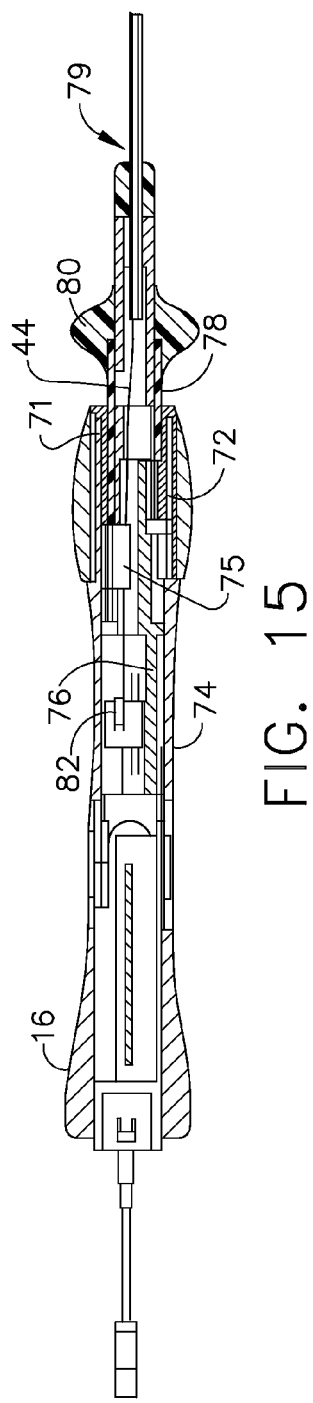
FIG. 15 is a side cross-sectional view of the control handle of FIG. 1, taken along line L-L.
Figure 16:
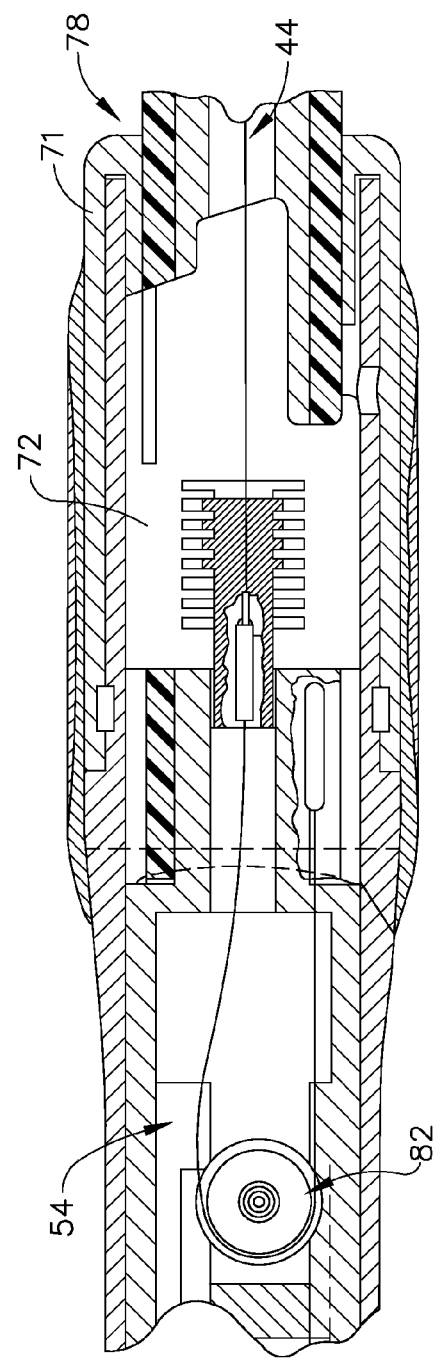
FIG. 16 is a partial detailed view of the control handle of FIG. 16.

In one embodiment, the catheter includes a control handle 16 as shown in FIGS. 15 and 16. The control handle 16 includes a deflection control assembly that has a handle body 74 in which a core 76 is fixedly mounted and a piston 78 is slidably mounted over a distal region of the core 76. The piston 78 has a distal portion that extends outside the handle body. A thumb knob 80 is mounted on the distal portion so that the user can more easily move the piston longitudinally relative to the core 76 and handle body 74. The proximal end of the catheter body 12 is fixedly mounted to the distal end of the piston 78. An axial passage 79 is provided at the distal end of the piston, so that various components, including lead wires 40, 41, contraction wire 44, deflection wire 54, sensor cable 46 and irrigation tubing 43 that extend through the catheter body 12 can pass into and if appropriate, through the control handle. For example, the lead wires 40, 41 can extend out the proximal end of the control handle 16 or can be connected to a connector that is incorporated into the control handle, as is generally known in the art.

The proximal end of the deflection wire 54 enters the control handle 16, and is wrapped around a pulley 82 and anchored to the core 76. Longitudinal movement of the thumb knob 80 and piston 78 distally relative to the handle body 74 and core 76 draws the proximal end of the deflection wire 54 distally. As a result, the deflection wire 54 pulls on the side of the intermediate section 14 to which it is anchored, thereby deflecting the intermediate section in that direction. To straighten the intermediate section 14, the thumb knob 80 is moved proximally which results in the piston 78 being moved proximally back to its original position relative to the handle body 74 and core 76.

The control handle 16 is also used for longitudinal movement of the contraction wire 44 by means of a rotational control assembly. In the illustrated embodiment, the rotational control assembly includes a cam handle 71 and a cam receiver 72. By rotating the cam handle in one direction, the cam receiver is drawn proximally to draw on the contraction wire 44. By rotating the cam handle in the other direction, the cam receiver is advanced distally to release the contraction wire. For example, where the helical form 22 has an original outer diameter of about 35 mm, tightening of the helical form by means of the contraction wire can reduce the outer diameter to about 20 mm. The contraction wire 44 extends from the catheter body 12 into the control handle 16, through the axial passage in the piston 78 and through the core 76 to be anchored in an adjuster 75 by which tension on the contraction wire can be adjusted.

In one embodiment, the position sensor 48 includes a plurality of single axis sensors ("SAS") carried on the cable 46 that extends through the first lumen 57 of the distal assembly 17 (FIG. 9), where each SAS occupies a known or predetermined position on the helical form 22. The cable 46 extends proximally from the distal assembly 17 through the central lumen of the transitional section 20, the fourth lumen 36 of the intermediate section 14 (FIG. 6), the central lumen 18 of the catheter body 12, and into the control handle 16. Each SA sensor can be positioned with a known and equal spacing separating adjacent SA sensors. In the disclosed embodiment, the cable carries three SASs that are positioned under the distal-most AR electrode, the proximal-most AR electrode, and a mid AR electrode, for sensing location and/or position of the helical form. Where the distal assembly carries ten AR electrodes, the SASs are under electrodes AR. The SASs enable the helical form to be viewed under mapping systems manufactured and sold by Biosense Webster, Inc., including the CARTO, CARTO XP and NOGA mapping systems. Suitable SASs are described in U.S. application Ser. No. 12/982,765, filed Dec. 30, 2010, the entire disclosure of which is incorporated herein by reference.

Figure 17A:
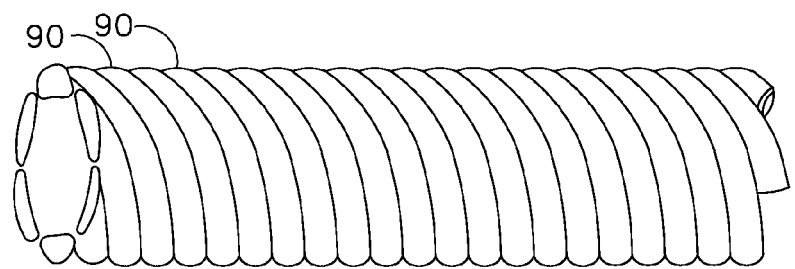
FIG. 17A is a side perspective view of a first embodiment of a hollow shape-memory support member.
Figure 17B:
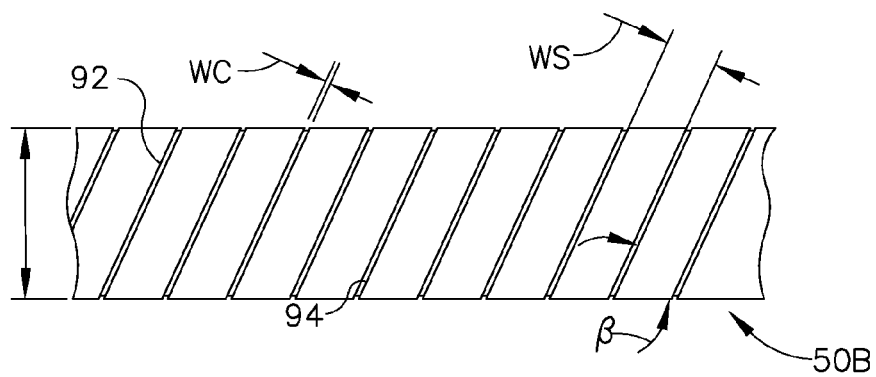
FIG. 17B is a side perspective view of a second embodiment of a hollow shape-memory support member.
Figure 17C:
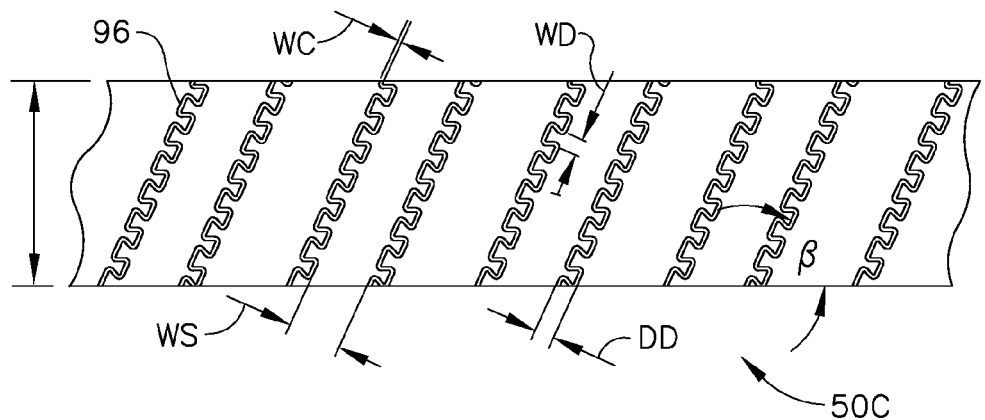
FIG. 17C is a side perspective view of a third embodiment of a hollow shape-memory support member.

In another alternative embodiment of the present invention, as illustrated in FIG. 2, the catheter has a distal assembly 17 whose helical form 22 can be varied by means of a stiffener or mandrel 84 that is extended through the shape memory support member 50 of the distal assembly. As illustrated in FIGS. 17A-17C, the shape memory support member 50 is tubular (but not necessarily with a circular cross-section) or otherwise hollow so as to be able to receive the mandrel whose shape and stiffness/flexibility differ from those of the support member 50. In one embodiment as shown in FIG. 17A, the hollow support member 50A includes multiple shape memory wires 90 that are coiled together forming a helical hollow strand tubing. Alternatively, a hollow support member 50B is formed from a tube with a spiral cut 92 (e.g., by laser) along the length of the member to provide greater flexibility. The cut is made at an angle between about 30-80 degrees, and preferably about 65 degrees, from the axial direction. As shown in FIG. 17B, the spiral cut can be made with a smooth and linear edge 94. In one detailed embodiment, the outer diameter of the member 50B is about 0.25 mm and the inner diameter is about 0.20 mm. The width of a strip WS between adjacent cuts is approx. 0.024 mm and the width of the cut WC is approx. 0.002 mm. Alternatively, as shown in FIG. 17C, the spiral cut can have an interlocking pattern 96, e.g., a dovetail pattern, so that the member can provide greater flexibility without elongation in the axial direction. In one detailed embodiment, the width of a strip WS between adjacent cuts is about 0.023 mm. The widest portion of each dovetail WD is about 0.005 mm and the depth of the dovetail DD is about 0.006 mm and the width of the cut WC is about 0.001 mm.

As illustrated in FIG. 3, the generally helical form 22 yields to assume the more expanded preformed shape of the mandrel 84 received therein and unwinds to a form with significantly less curvature (shown in solid lines). Upon removal of the mandrel 84 from the distal assembly 17, the helical form 22 reassumes the predetermined shape of the shape memory support member 50 (shown in broken lines).

It is understood that in these embodiments, the hollow support member 50 can extend proximally to at least a proximal portion of the catheter body 12 that remains outside of the patient, if not through control handle 16 so the proximal end is accessible to the operator for inserting the mandrel. The proximal end can exit the catheter body at a location near the control handle or it can extend through the control handle and exit the proximal end of the control handle to be accessed by the operator.

Thus, the operator can expand or even significantly straighten the form of the distal assembly by advancing the mandrel 84 through the hollow support member 50A, 50B, 50C where the mandrel is straighter and stiffer than the hollow shape-memory member. In that regard, it is understood that by providing a mandrel that is stiffer than the shape-memory member of the form of the distal assembly, the form can generally assume the configuration or shape of the mandrel over the configuration of the shape-memory member.

The present catheter 10 is a steerable, multi-electrode, irrigated luminal catheter. The catheter is deployed in a target region of the body, e.g., the atria of the heart or the renal artery or other anatomical structure, through a guiding sheath. The catheter is designed to facilitate electrophysiological mapping of the target region, e.g., the atria, and to transmit energy, e.g., radiofrequency (RF) current, to the catheter electrodes for ablation purposes, for example, to denervate heart tissue or the renal nerves. For ablation, the catheter is used in conjunction with a multi-channel RF generator and irrigation pump.

The configuration of the catheter permits the catheter to make consistent circumferential contact with the tissue inside the vessel. Intracardiac signals are recorded by an EP Recording System and the location of the catheter is visualized by fluoroscopy. Once the catheter is in the desired location, energy is delivered (to multiple electrodes simultaneously or selectively) to the vessel in unipolar or bipolar mode resulting in denervation of the vessel.

In one embodiment, ablation is delivered at a set wattage on the multi-channel RF generator. During ablation the multi-channel RF generator monitors the temperature of the ring electrode(s) involved and reduces the wattage if the temperature exceeds a value set by the user. The multi-channel RF generator routes the RF current through the selected ring electrodes and catheter temperature information is sent from the thermocouple on the catheter to the generator.

During ablation, an irrigation pump is used to deliver normal heparinized saline to the ring electrodes to cool the ring electrodes to prevent blood from coagulating. The apertures in the ring electrodes facilitate irrigation of the ablation areas of the catheter. Where deeper lesions are desired, the greater flow distribution (without greater flow rate) of each ring electrode via the apertures reduces the increased risk of charring and coagulum on the ablation surfaces that would normally be encountered when the amount of power delivered to the electrode/tissue interface is increased. A greater flow distribution from each ring electrode which leads to improved irrigation efficiency offers advantages, including (1) higher power delivery without increasing fluid pump flow rate, (2) ability to use currently available, flow rate-limited pumps, (3) eliminate need to use multiple pumps, and/or (4) reduction in fluid load on patient during ablation procedure.

Figure 18:
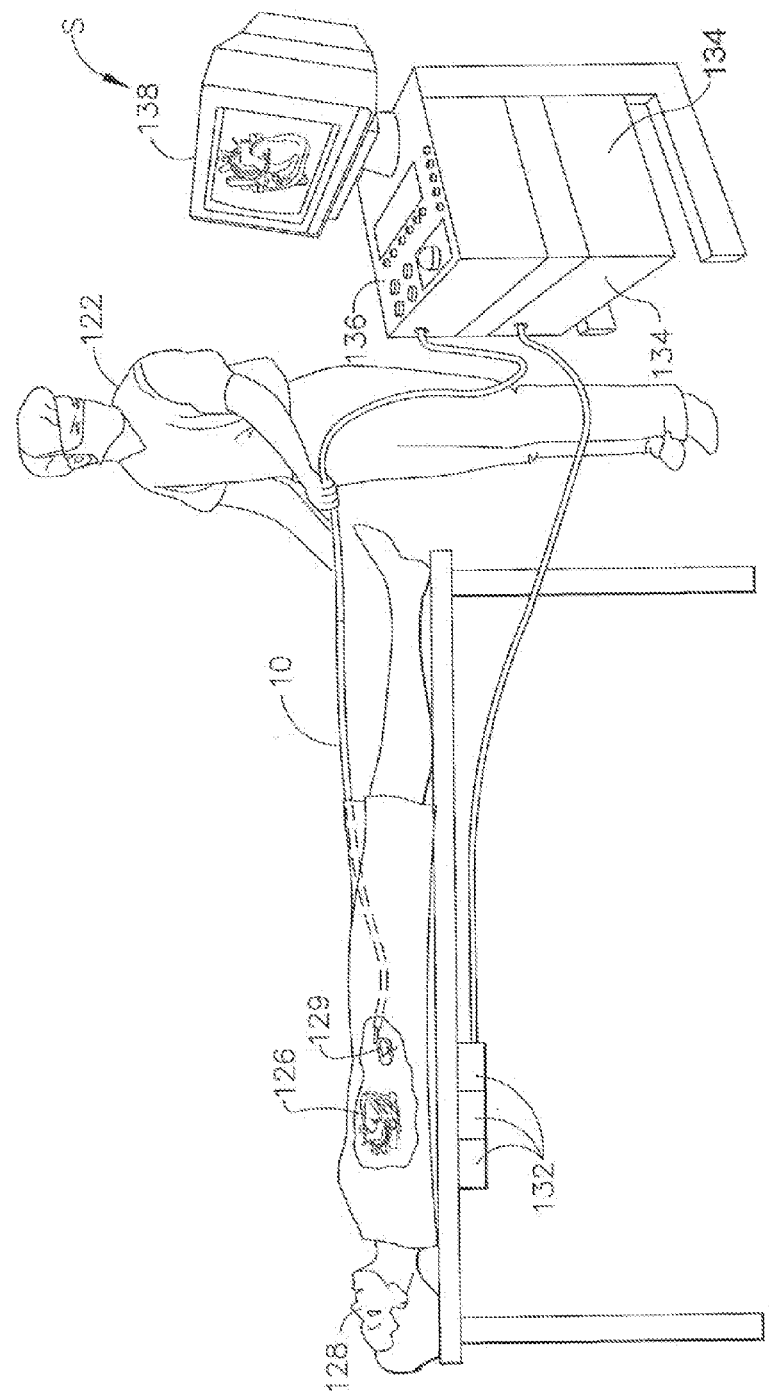
FIG. 18 is a schematic pictorial illustration of a system for ablation of tissue in the heart, in accordance with an embodiment of the present invention.
Figure 19:
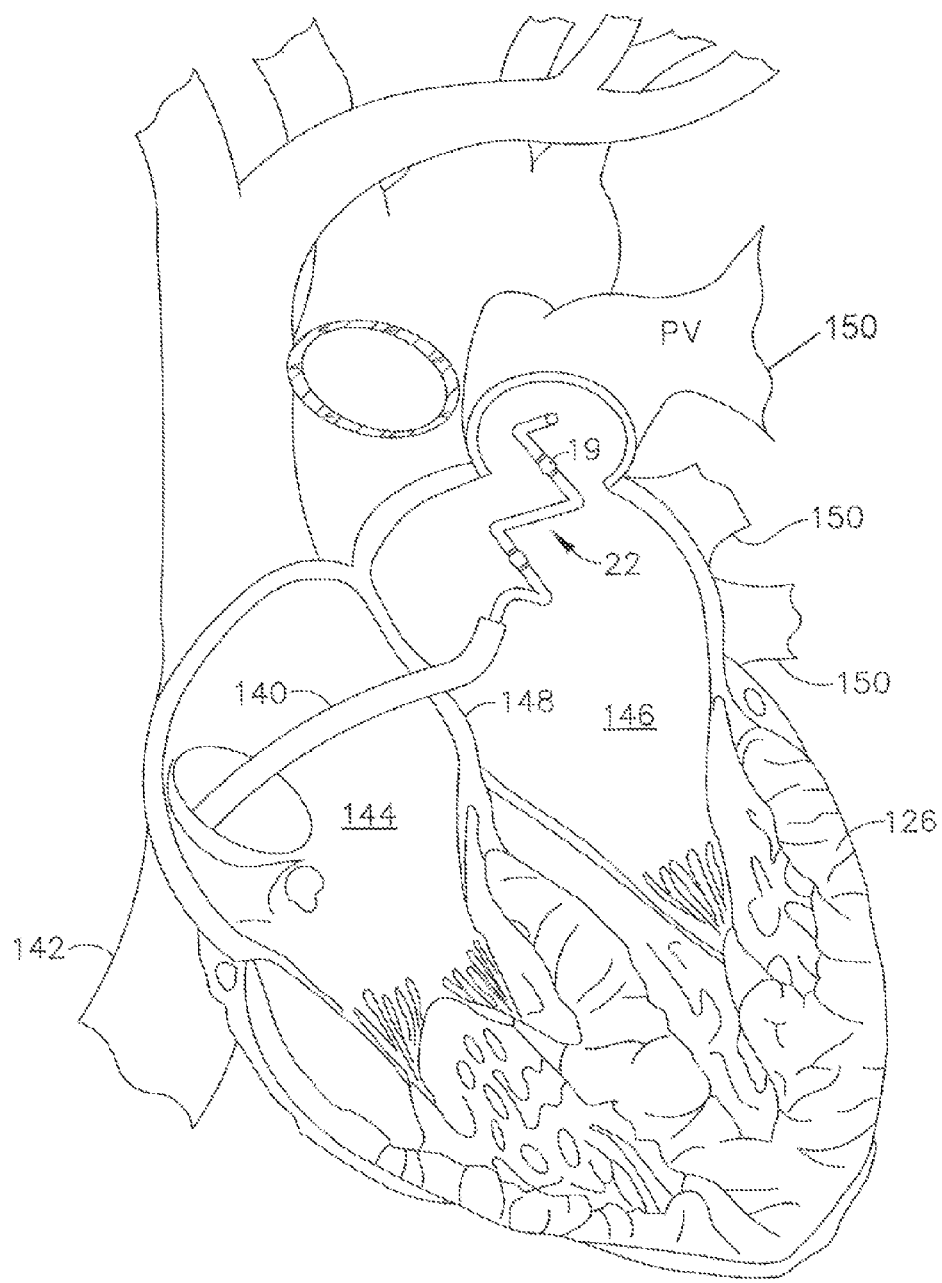
FIG. 19 is a schematic sectional view of a heart showing insertion of a catheter into the left atrium and the pulmonary vein, in accordance with an embodiment of the present invention.
Figure 20:
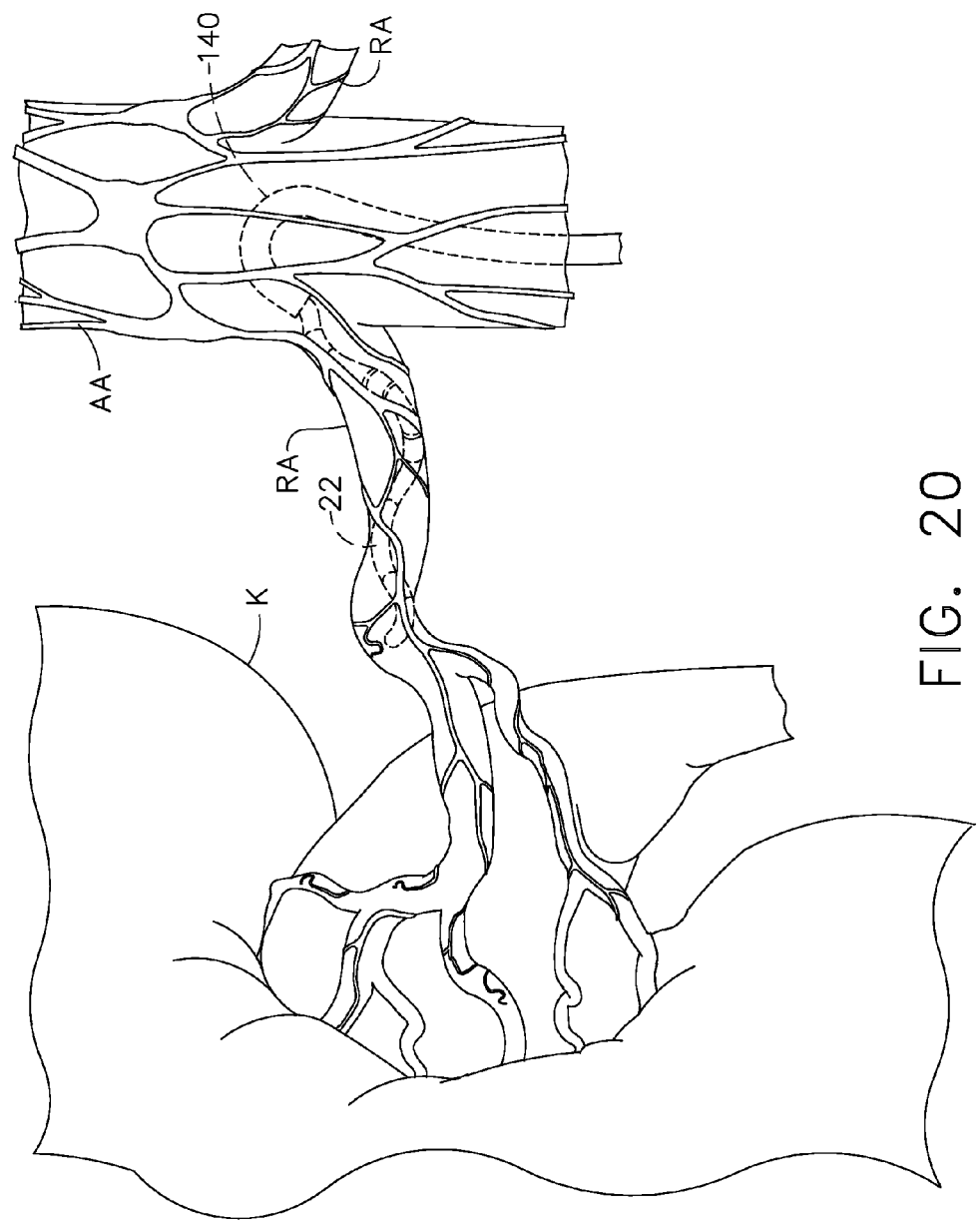

FIG. 18 is a schematic pictorial illustration of a system S for ablation of tissue in a heart 126 or renal anatomy 129 of a patient 128, in accordance with an embodiment of the present invention. Referring to FIGS. 19-21, an operator 122, such as a cardiologist, electrophysiologist or interventional radiologist, inserts a catheter 10 made in accordance with the present invention and described in through the vascular system of the patient (usually starting at a puncture in the femoral artery) so that the distal end of the catheter enters a chamber of the patient's heart or the abdominal aorta (AA) near one of the renal arteries (RA) which provides blood flow to kidney (K). Operator advances the catheter so that the distal assembly 117 of the catheter engages endocardial tissue at a desired location or locations, as shown in FIG. 21. Catheter 10 is connected by a suitable connector at its proximal end to a console 136. The console comprises an RF generator for applying RF energy through electrodes on the end section of the catheter in order to ablate the tissue contacted by the distal section. Alternatively or additionally, catheter may be used for other diagnostic and/or therapeutic functions, such as intracardiac electrical mapping or other types of ablation therapy.

In the pictured embodiment, system S uses magnetic positioning sensing to determine position coordinates of the distal assembly of the catheter inside heart. To determine the position coordinates, a driver circuit 134 in console 136 drives field generators 132 to generate magnetic fields within the body of patient. Typically, field generators comprise coils, which are placed below the patient's torso at known positions external to the body. These coils generate magnetic fields in a predetermined working volume that contains heart. One or more magnetic field sensors within the end section of catheter generate electrical signals in response to these magnetic fields. The console 136 processes these signals in order to determine the position (location and/or orientation) coordinates of the distal assembly 117 of the catheter, and possibly also the deformation of the distal assembly, as explained below. Console may use the coordinates in driving a display 138 to show the location and status of the catheter. This method of position sensing and processing is described in detail, for example, in PCT International Publication WO 96/05768, whose entire disclosure is incorporated herein by reference, and is implemented in the CARTO system produced by Biosense Webster Inc. (Diamond Bar, Calif.).

Alternatively or additionally, system may comprise an automated mechanism (not shown) for maneuvering and operating catheter within the body of patient. Such mechanisms are typically capable of controlling both the longitudinal motion (advance/retract) and the rotation of catheter. In such embodiments, console generates a control input for controlling the motion of the catheter based on the signals provided by the position sensing system.

Although FIG. 18 shows a particular system configuration, other system configurations may be used in alternative embodiments of the present invention. For example, the methods described hereinbelow may be applied using position transducers of other types, such as impedance-based or ultrasonic position sensors. The term "position transducer" as used herein refers to an element mounted on or in catheter that causes console to receive signals indicative of the coordinates of the element. The position transducer may thus comprise a receiver in the catheter, which generates a position signal to the control unit based on energy received by the transducer; or it may comprise a transmitter, emitting energy that is sensed by a receiver external to the probe. Furthermore, the methods described hereinbelow may similarly be applied in mapping and measurement applications using not only catheters, but also probes of other types, both in the heart and in other body organs and regions.

FIG. 19 is a schematic sectional view of heart 126, showing insertion of catheter 10 having helical form 22 into the heart, in accordance with an embodiment of the present invention. To insert the catheter in the pictured embodiment, the operator first passes a sheath 140 percutaneously through the vascular system and into right atrium 144 of the heart through ascending vena cava 142. The sheath penetrates through interatrial septum 148, typically via the fossa ovalis, into left atrium 146. Alternatively, other approach paths may be used. Catheter is then inserted through the sheath until a distal assembly 117 of the catheter passes out of the distal opening of the end of the sheath 140 into the left atrium 146.

Operator aligns the longitudinal axis of sheath 140 (and of catheter) inside left atrium 146 with the axis of one of pulmonary veins 150. He may use the thumb knob 80 of the control handle 16 to deflect the intermediate section 14 in directing the distal assembly 117 toward the target vessel. The operator may carry out this alignment using the position sensing methods described above, along with a pre-acquired map or image of heart. Alternatively or additionally, the alignment may be performed under fluoroscopic or other means of visualization. The operator advances the catheter toward the target pulmonary vein 150 (PV) so that the distal assembly 117 contacts the wall of the pulmonary vein 150 (PV). By manipulating the cam handle 71, the helical form of the distal assembly 117 is expanded or contracted to fit inside the pulmonary vein 150 (PV) and contact the wall. In the disclosed embodiment, the contraction wire 44 is drawn proximally by the cam receiver 72 to tighten and decrease the diameter of the helical form when the cam handle is turned in one direction. By turning the cam handle in the opposition direction, the cam receiver releases the contraction wire to allow the helical form to expand and return to its original diameter.

The operator can then rotate the catheter about its axis within the sheath so that the distal assembly traces an annular path around the inner circumference of the vein. Meanwhile, the operator actuates RF generator to ablate the tissue in contact with the AR electrodes along the path. Simultaneously or in between RF pluses, impedance and/or PV potential recordings can be made with the electrodes. After completing this procedure around one pulmonary vein, the operator may shift the sheath and catheter and repeat the procedure around one or more of the other pulmonary veins.

A similar procedure is used in FIGS. 20 and 21 to ablate tissue inside the renal artery (RA) in order to denervate the renal nerves that are present in the artery. Operator aligns the longitudinal axis of sheath 140 (and of catheter) inside abdominal aorta AA with the axis of one of renal arteries (RA). He may use the thumb knob 80 of the control handle 16 to deflect the intermediate section 14 in directing the distal assembly 117 toward the target artery. The operator may carry out this alignment using the position sensing methods described above, along with a pre-acquired map or image of the renal anatomy. Alternatively or additionally, the alignment may be performed under fluoroscopic or other means of visualization. The operator advances the catheter toward the target renal artery vein so that the distal assembly 117 enters the artery. By manipulating the cam handle 71, the helical form of the distal assembly 117 is contracted or expanded to fit inside the renal artery RA) and to cause ring electrodes 19 to touch the wall of the renal artery. In the disclosed embodiment, the contraction wire 44 is drawn proximally by the cam receiver 72 to tighten and decrease the diameter of the helical form when the cam handle is turned in one direction. By turning the cam handle in the opposition direction, the cam receiver releases the contraction wire to allow the helical form to expand and return to its original diameter.

The operator can then rotate the catheter about its axis within the sheath so that the distal assembly traces an annular path around the inner circumference of the artery. Meanwhile, the operator actuates RF generator to ablate the tissue in contact with the AR electrodes along the path. Simultaneously or in between RF pulses, impedance and/or PV potential recordings can be made with the electrodes. After completing this procedure around one pulmonary vein, the operator may shift the sheath and catheter and repeat the procedure inside the other renal artery.

Figures 22, 23:
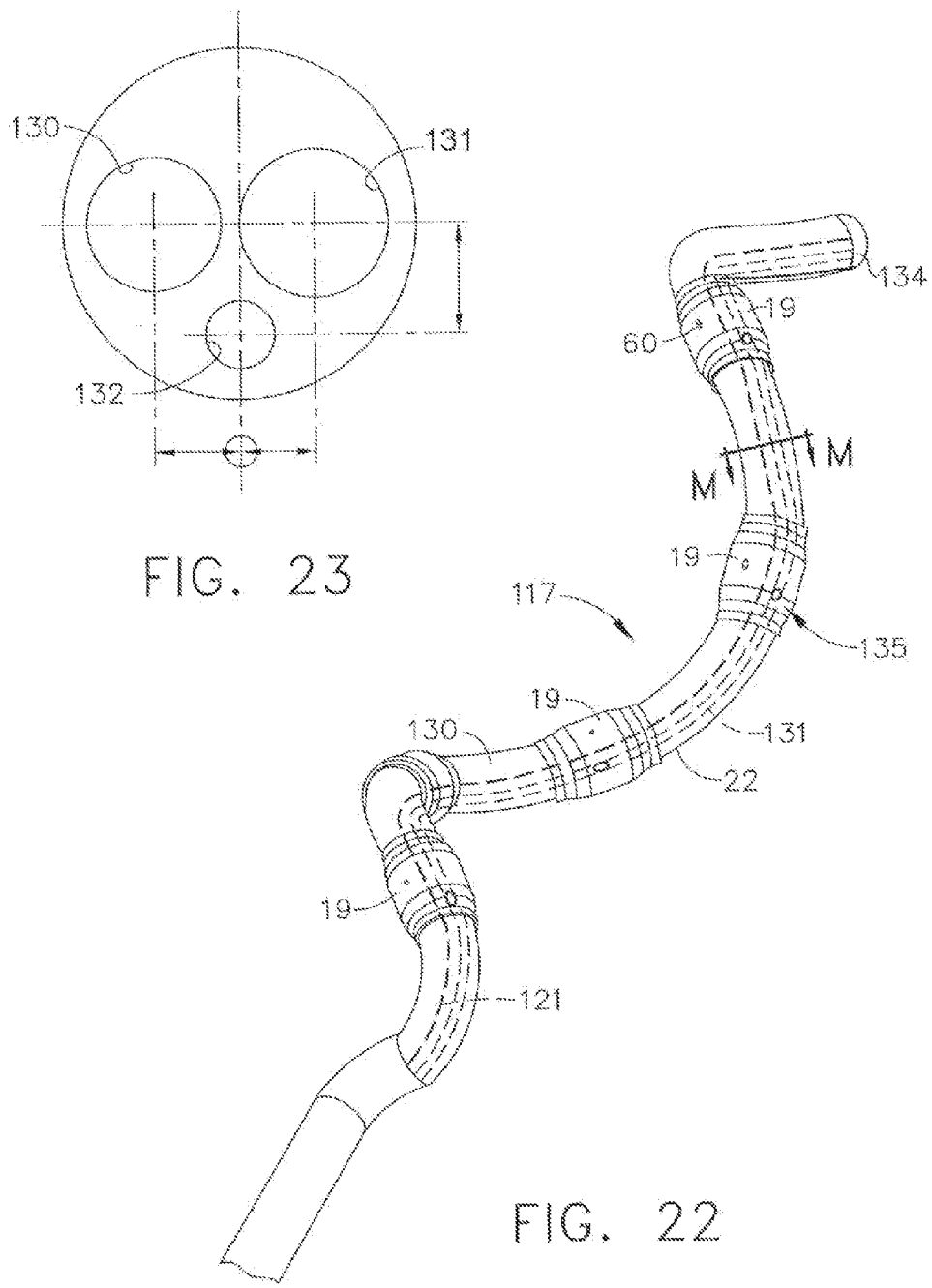
FIG. 22 is a perspective view of the distal assembly of a catheter in accordance with the present invention.
FIG. 23 is a cross-section of the distal assembly of FIG. 22 through line M-M.

FIG. 22 is a perspective view of another embodiment of a distal assembly of a catheter in accordance with the present invention. Distal assembly 117 comprises a plurality of electrodes 19 having a plurality of apertures 69 as described above), and a multi-lumen tube 125 having an irrigation lumen 130 and a lead wire lumen 131 for the thermocouple/rf wires which thermocouples 135 are mounted at or near the outermost diameter of the electrodes and at the outermost diameter of the helical shape for tissue contact. An additional lumen 132 houses the nitinol wire 121 provides the shape to the helix when it is unconstrained by a sheath, mandrel or guidewire. The dome 136 is provides an atraumatic tip and also an anchor for the nitinol helix 121. The nitinol helix extends into the tip of the distal assembly distal the distal most electrode 19 which tip provides a leader for positioning the catheter into the PV, renal artery, renal vein or other vessel.

FIG. 23 is a cross-section of the distal assembly of FIG. 22 through M-M showing multi-lumen tube 125 with irrigation lumen 130, nitinol helix lumen 132 and lead wire lumen 131.

Figure 24A:
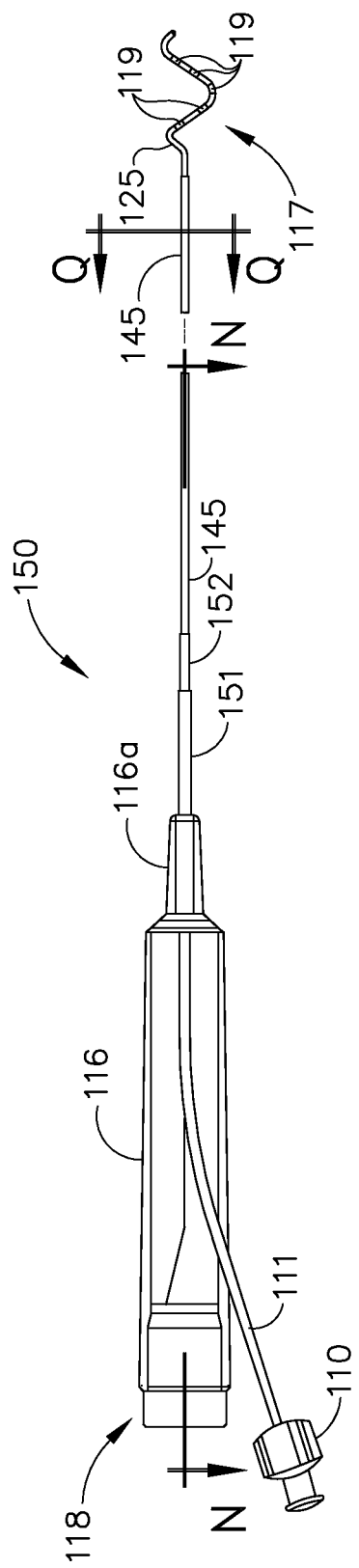
FIG. 24 A is a side view of an additional embodiment of the present invention having a helical distal end portion for treatment of vessels.
FIG. 24B is a cross-sectional view of a proximal portion of FIG. 24A through line N-N.
Figure 24B:
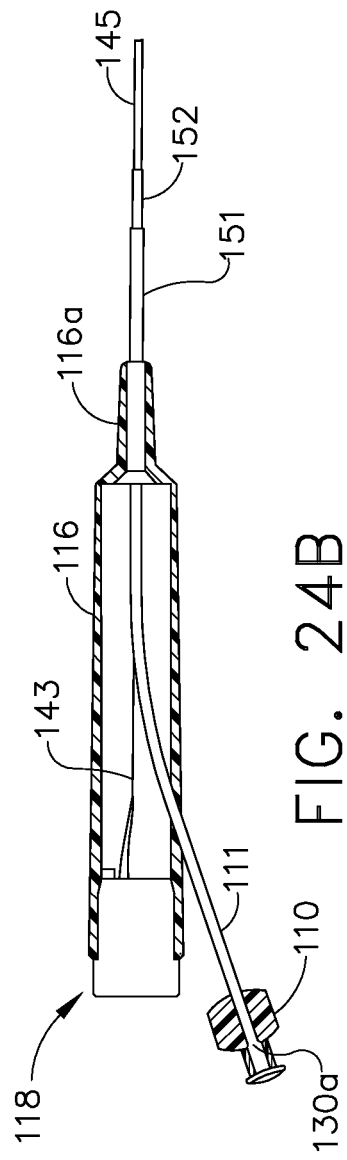

FIG. 24A is a side view of an alternative embodiment of a catheter in accordance with the present invention. FIG. 24B is a cross-sectional view of the proximal portion of FIG. 24A through line N-N. Control handle 116 is a generally cylindrical tubular structure but can also take other shapes and configurations that provide the user of the device with the ability to manipulate the catheter while providing an interior cavity for passage of components. Control handle 116 is made of an injection molded polymer such as polyethylene, polycarbonate or ABS or other similar material. Connector 118 is inserted into the proximal end of control handle 116 and provides an electrical connection to a mating connector and cable assembly that is connected to an RF generator. Connector 118 is secured through the use of epoxy or other similar means. Lead wire assembly 143 comprises a Teflon sheath and five pairs of lead wires 40, 41 housed therein, one pair for each thermocouple 135 and ring electrode 19. The proximal end of each lead wire is electrically and mechanically connected to the connector 118 through the use of solder or other means. Irrigation luer hub 110 is a fitting capable of being attached to mating connector from an irrigation source such as an irrigation pump (not shown). Irrigation luer hub 110 is attached to irrigation side arm 111 using polyamide to form a seal against fluid intrusion. Irrigation fluid is then conveyed from the irrigation hub through the irrigation lumen 130a. Irrigation lumen 130a passes through the lumen in side arm 111 through the wall of the control handle 116 through the shaft 145 into the multi-lumen tube 125 for approximately 3 mm into the irrigation lumen 130 in multi-lumen tube 125 of distal assembly 117 in order to convey irrigation fluid to each ring electrode 19 which has a plurality of holes therethrough.

Control handle 116 has a portion which of a smaller diameter 116a which is adapted to receive the proximal end of the catheter assembly 150 which is comprised of strain relief element 151, 152 and shaft 145 through which lead wire assembly 143 and irrigation lumen 130a pass. Strain relief elements 151 and 152 in the preferred embodiment are two shrink sleeves made of polyolefin or similar material which are heated to shrink over the shaft 145. Polyurethane is then used to attach the strain relief elements 151 and 152 into the handle portion 116a.

The working length (L) of the catheter assembly 150 is approximately 90 cm from the distal end of strain relief element 152 to the distal tip of the distal assembly 117 when used for renal ablation. The working length may vary depending on the application. Distal assembly 117 comprises a multi-lumen tube 125 which has a plurality of ring electrodes 19 mounted thereon. In a preferred embodiment for renal ablation five ring electrodes are used each having an electrode length (W) of 3 millimeters and an inter-electrode spacing (S) of 4 millimeters. The maximum diameter of the helix is approximately 10 mm when un-constricted. The ring electrodes 19 preferably have a maximum outer diameter of 2 mm at the middle and a minimum outer diameter of 1.7 mm at the narrower ends. The ring electrodes may be made on any material described herein but are preferably made of 90% platinum and 10% iridium but cold be comprised a combination of these and/or other suitable noble metals such as gold and palladium. Multi-lumen tube 125 is made of a material that is more flexible than the material in the shaft 145 preferably multi-lumen tube 125 is made of 35D PEBAX with no wire braid although other materials and durometers may be used depending on the desired stiffness of the distal assembly. Shaft 145 is made of pellethane, polyurethane or PEBAX and contains an internal stiffener as described herein which is an inner tube made of nylon or polyimide or similar material.

Figure 25B:
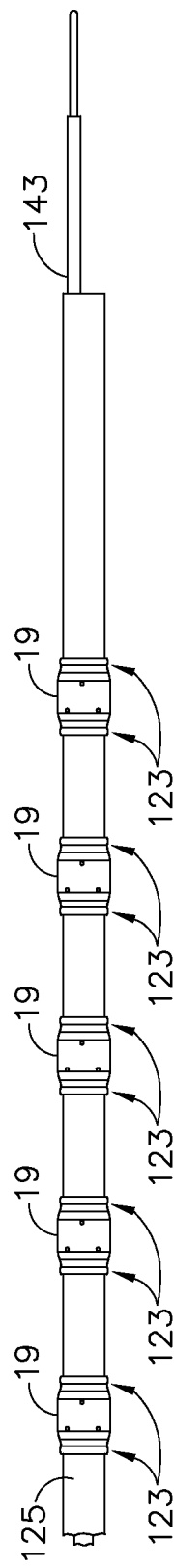
FIGS. 25A and 25B are a side view and partially transparent side view of the electrode bearing portion of the distal assembly of the embodiment of FIG. 24A.
Figure 25A:
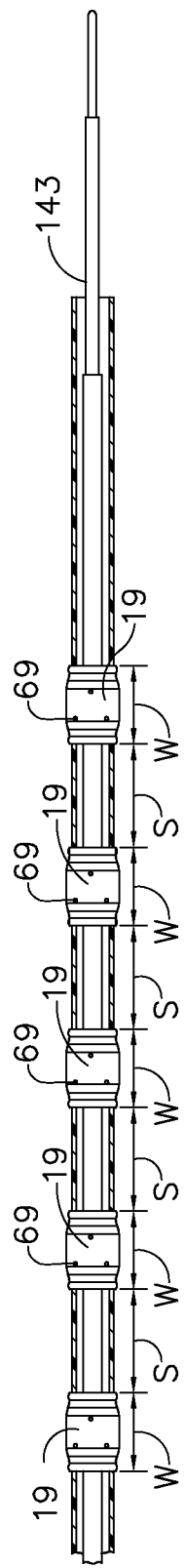
Figure 27:
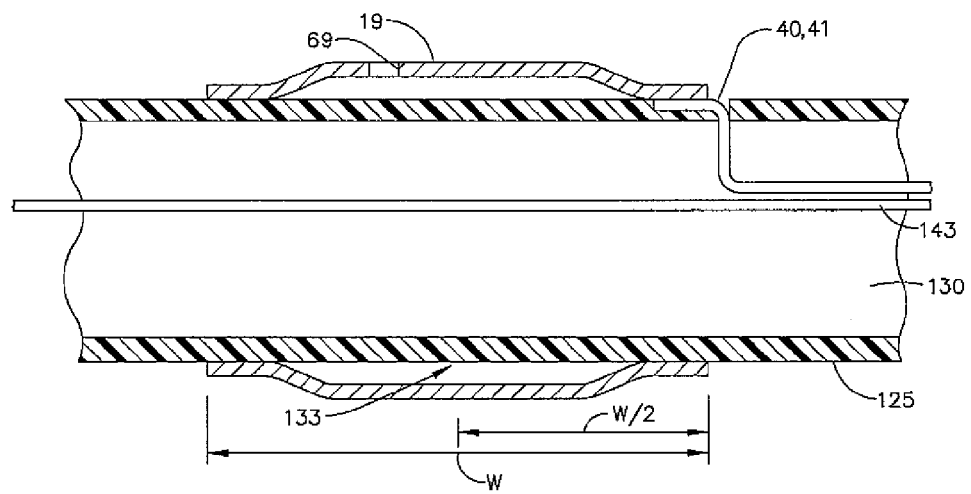
FIG. 27 is a cross-sectional view of FIG. 25B through line R-R.

FIGS. 25A and 25B show a portion of the distal assembly 117 containing the ring electrodes 19 each having a preferable length (W) of approximately 3 mm and an inter-electrode spacing (S) of approximately 4 millimeters. Each pair of lead wires 40 and 41 are welded to a respective ring electrode to provide a robust connection (further depicted in FIG. 27). Polyurethane coating 123 is placed over each end of each ring electrode in order to seal against a fluid intrusion and to provide an atraumatic transition between the electrodes 19 and the multi-lumen tube 125 of distal assembly 117. In FIG. 25B the polyurethane coating 123 is not depicted and multi-lumen tube 125 is shown transparent so as to show the placement of the lead assembly 143 which at this point comprises the five pairs of lead wires (40, 41) and a polyamide coating over the bundle of wires. In FIG. 27 the welded connection of a pair of lead wires (40, 41) to a specific ring electrode 19 is shown. Also, the cross-sectional area of the gap between the wall portion of the ring electrode 19 having the greater outer diameter and the multi-lumen tube 125 can be seen. This gap is the space through which irrigation fluid flows from the irrigation lumen 130 through breach hole 133 to the holes in the wall of ring electrode 19. The breach hole 133 should be positioned at about the half-way (W/2) point along the length of the ring electrode 19.

Figure 26A:
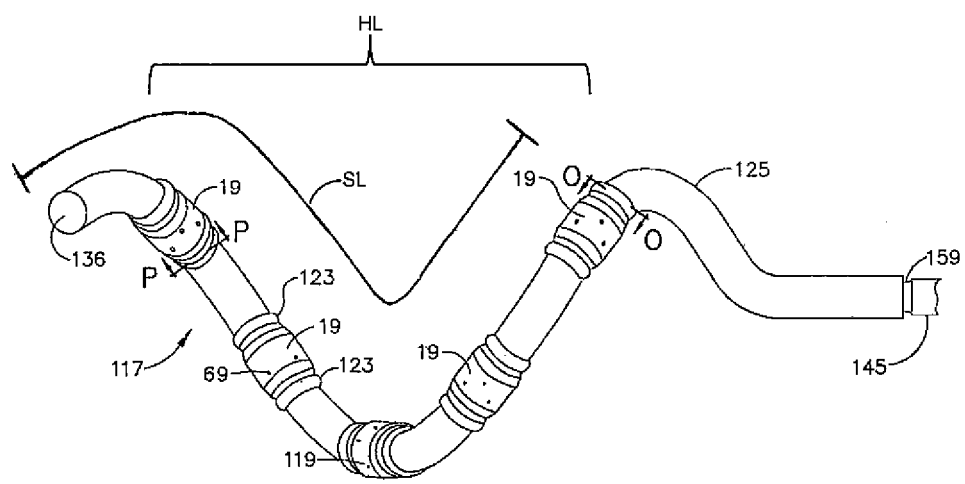
FIG. 26 A is a perspective view of the distal assembly of the embodiment of FIG. 24A.
FIG. 26B is a cross-sectional view of the distal assembly of FIG. 26A taken through line O-O.
FIG. 26C is a cross-sectional view of the distal assembly of FIG. 26A taken through line P-P.
FIG. 26D is a cross-sectional view of the distal assembly of FIG. 26A taken through line Q-Q.
Figure 26D:
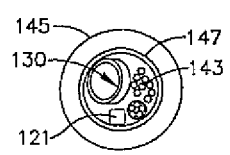
Figure 26B:
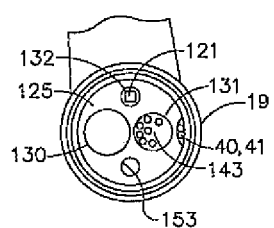
Figure 26C:
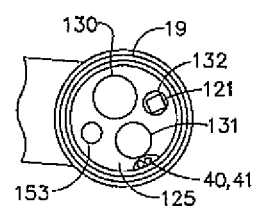

FIGS. 26A-D show the distal assembly 117 connected to shaft 145 and various cross-sections therethrough. FIG. 26B is a cross-sectional view of FIG. 26A through O-O. FIG. 26C is a cross-sectional view of FIG. 26A though line P-P. FIG. 26D is a cross-sectional view through line Q-Q in shaft 145 in FIG. 24A. Atraumatic tip dome 136 is a polyurethane dome with a shaft that extends into the end of the irrigation lumen 130 at the end of the multi-lumen tube 125. The nitinol wire/shape memory support member 121 extends from at or near the distal end of the multi-lumen tube 125 into the shaft 145 for approximately 25 millimeters into the shaft. This provides stability to the distal assembly 117. Nitinol wire 121 is preferably square in cross-section 0.009 inch by 0.009 inch) but could be square, circular or rectangular in cross-section with a width or diameter between 0.006 inch and 0.012 inch. The nitinol wire is pre-formed to take a helical shape having a diameter of approximately 10 mm and a helical shape length (HS) of approximately 20 mm electrode edge to edge when it is in not constrained within a sheath and a straight length (SL) of approximately 36 mm proximal edge of most proximal ring electrode 19 to the distal tip when constrained in a sheath. The nitinol wire will impart this helical shape on the other components of distal assembly 117. In FIGS. 26B and 26C the cross-sections of multi-lumen tube 125 shows ring electrode 19 mounted on multi-lumen tube 125. Multi-lumen tube 125 also contains an irrigation lumen 130 and a lead wire lumen 131 housing the lead wire assembly 143 having a pair of lead wires 40, 41 for each electrode. In FIG. 26B the connection of a first pair of lead wires (40, 41) to electrode 19 is shown. The additional pairs of lead wires can be seen in the remainder of lead wire assembly 143 in FIG. 26B. FIG. 26C shows the final pair of lead wires (40, 41) attached to the distal most electrode 19. Lumen 132 houses the nitinol wire 121. Lumen 153 is in multi-lumen tube 125 is unused in the preferred embodiment but could be used for wiring for additional thermocouples or other sensors that are desired in the tip assembly. In FIG. 26D the arrangement of the nitinol wire 121, irrigation lumen 130 and the lead wire assembly 143 within the shaft 145 can be seen. Stiffener 147 provides added stiffness to the shaft 145 and is comprised of a material such as polyimide or nylon, preferably polyimide having a thickness of approximately 0.002 thousandths. The stiffener 147 runs substantially the entire length of the shaft 145. In FIG. 26A the polyurethane bond 159 of the shaft 145 and the multi-lumen tube 125 is depicted. This preferred polyurethane bond 159 prevents fluids from entering at the junction of these two elements. Other methods of bonding such as heat sealing or other glues may be used.

In use, the catheter assembly 150 depicted in FIGS. 24A-B, FIGS. 25A-B, FIGS. 26A-D and FIG. 27 is used with a sheath, preferably, a steerable sheath (not shown) which facilitates the placement of the catheter in the proper place in the anatomy for the desired ablation/denervation. Once the catheter assembly 150 exits the sheath the nitinol wire/support member 121 will cause the distal assembly to take the pre-configured helical shape. The 10 mm diameter helical shape will provide sufficient apposition of the ring electrodes against the interior wall of the renal artery to provide contact for an ablation that upon the delivery of RF energy from a generator to one or more of the ring electrodes will result in the denervation or partial denervation of the artery.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Any feature or structure disclosed in one embodiment may be incorporated in lieu of or in addition to other features of any other embodiments, as needed or appropriate. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
an elongated body having a longitudinal axis and proximal and distal ends;
a distal assembly mounted on the distal end of the elongated body, the elongated body and distal assembly being configured for insertion into a renal artery, the distal assembly including a shape-memory support member, and having a helical form with a pitch ranging between 0.5 cm and 1.9 cm and a diameter ranging between 4 mm and 10 mm, the helical form including a plurality of turns and subtending greater than 520 degrees, the helical form being oriented at an oblique angle of about 30 degrees to about 60 degrees relative to the longitudinal axis when unconstrained;
at least one irrigated ablation ring electrode mounted on the distal assembly, wherein the shape-memory support member is preformed with a helical shape having a diameter of about 10 mm and a helical shape length of about 20 mm electrode edge to edge, and a generally straight length of about 36 mm from a proximal edge of a most proximal ring electrode of the at least one ring electrode to a distal tip of the distal assembly; and
a control handle mounted at the proximal end of the elongated body.

2. The catheter of claim 1, further comprising a contraction wire extending through the elongated body and the distal assembly, wherein the control handle includes a first control member configured to actuate the contraction wire to contract the helical form.

3. The catheter of claim 1, further comprising a deflection wire extending through the elongated body, wherein the control handle includes a second control member configured to actuate the deflection wire to deflect a portion of the elongated body.

4. The catheter of claim 1, wherein the shape-memory support member has a square cross-section.

5. The catheter of claim 4, wherein the shape memory support member width and length of the square are between six and twelve thousandths of an inch.

6. The catheter of claim 5, wherein the shape memory support member width and length of the square are nine thousandths of an inch.

7. The catheter of claim 1, wherein the shape memory support member has a lumen and the catheter further comprises a mandrel adapted for insertion through the lumen in the shape-memory support member, wherein the mandrel has a different form from the helical form.

8. The catheter of claim 1, wherein at least one of the at least one irrigated ablation ring electrode has at least one aperture configured to pass fluid from inside the ring electrode to outside the ring electrode in a radial direction.

9. The catheter of claim 1, wherein at least one of the at least one irrigated ablation ring electrode has at least one aperture configured to pass fluid from inside the ring electrode to outside the ring electrode in an axial direction.

10. The catheter of claim 1, wherein at least one of the at least one ring electrode is connected to an electrical lead capable of providing a signal indicative of a measure of temperature.

11. The catheter of claim 10, wherein the electrical lead is connected to a thermocouple mounted on the connected ring electrode near the outer diameter of the connected ring electrode and near the outer diameter of the helical form.

12. The catheter of claim 1, further comprising a luer hub near the control handle and an irrigation lumen that extends from the luer hub distally through the elongated body and into the distal assembly to provide irrigation fluid to the at least one ring electrode.

13. The catheter of claim 12, wherein the luer hub is attached to the control handle by an irrigation side arm having a lumen, and the irrigation lumen passes through the side arm lumen into the control handle.

14. The catheter of claim 1, wherein the at least one irrigated ablation ring electrode comprises five ring electrodes.

15. The catheter of claim 1, wherein the shape memory support member extends proximally of the distal assembly into the elongate body.

16. The catheter of claim 15, wherein the shape-memory support member extends proximally of the distal assembly into the elongate body approximately 25 millimeters.

17. The catheter of claim 1, wherein the helical form is oriented at an oblique angle of about 45 degrees relative to the longitudinal axis when unconstrained.

18. A catheter comprising:
an elongated body having a longitudinal axis;
a distal assembly distal the elongated body, the distal assembly and elongated body being configured for insertion into a renal artery, the distal assembly having a hollow support member defining a first predetermined form of the distal assembly, the first form having a helical form with a pitch ranging between 0.5 cm and 1.9 cm and a diameter ranging between 4 mm and 10 mm, the helical form including a plurality of turns and subtending greater than 520 degrees, the turns of the helical form being oriented at an oblique angle of about 30 degrees to about 60 degrees relative to the longitudinal axis when unconstrained;
at least one electrode mounted on the distal assembly, wherein the support member is preformed with a helical shape having a diameter of about 10 mm and a helical shape length of about 20 mm electrode edge to edge, and a generally straight length of about 36 mm from a proximal edge of a most proximal electrode of the at least one electrode to a distal tip of the distal assembly;
a control handle proximal the elongated body; and
a mandrel defining a second predetermined form, the mandrel being adapted for insertion into the hollow support member.

19. The catheter of claim 18, wherein the first predetermined form of the distal assembly has a greater curvature than the second predetermined form.

20. The catheter of claim 18, wherein the first predetermined form has an on-axis configuration such that a central longitudinal axis of the first predetermined form is axially aligned with the longitudinal axis of the elongated body.

21. The catheter of claim 18, wherein the first predetermined form of the distal assembly has an off-edge configuration such that the first predetermined form has a central longitudinal axis that is parallel without axial alignment with a longitudinal axis of the elongated body.

22. The catheter of claim 18, wherein the hollow support member includes a hollow strand tubing.

23. The catheter of claim 18, wherein the hollow support member includes a tubular member with a spiral cut along a length of the tubular member.

24. The catheter of claim 23, wherein the spiral cut includes an interlocking pattern.

25. A catheter comprising:
an elongated shaft having a longitudinal axis;
a distal assembly distal the elongated shaft, the distal assembly and the elongated shaft being configured for insertion into a renal artery, the distal assembly having a shape-memory support member and a generally helical form, the generally helical form of the distal assembly having a pitch ranging between 0.5 cm and 1.9 cm and a diameter ranging between 4 mm and 10 mm, the helical form having a plurality of turns and subtending greater than 520 degrees when unconstrained, the helical form being oriented at an oblique angle of about 30 degrees to about 60 degrees relative to the longitudinal axis when unconstrained;
at least two irrigated ablation ring electrodes mounted on the generally helical form, each electrode having a length, wherein the shape-memory support member is preformed with a helical shape having a diameter of about 10 mm and a helical shape length of about 20 mm electrode edge to edge, and a generally straight length of about 36 mm from a proximal edge of a most proximal ring electrode of the at least one ring electrode to a distal tip of the distal assembly;
a control handle proximal the elongated shaft; and
wherein the at least two irrigated ring electrodes are mounted a distance apart which is greater than the length of the electrodes.

26. The catheter of claim 25, wherein the helical form has an on-axis configuration such that a central longitudinal axis of the helical form is axially aligned with the longitudinal axis of the elongated shaft.

27. The catheter of claim 25, wherein the distal assembly includes a multi-lumen tube having a first irrigation lumen, a nitinol wire lumen for the shape-memory support member and a lead wire lumen.

28. The catheter of claim 27, the distal assembly having a breach hole from the first irrigation lumen through the wall of the multi-lumen tube, the breach hole configured to allow passage of irrigation fluid from the first irrigation lumen to at least one of the at least two irrigated ablation ring electrodes.

29. The catheter of claim 27, further comprising a luer hub near the control handle and a second irrigation lumen that extends from the luer hub distally through the elongated shaft and into the first irrigation lumen in the multi-lumen tube to provide irrigation fluid to at least one of the at least two ring electrodes.

30. The catheter of claim 25, wherein the shape-memory support member is a nitinol wire having a square cross-sectional shape.

31. The catheter of claim 30, wherein the shape-memory support member extends proximally of the distal assembly into the elongated shaft.

32. The catheter of claim 31, wherein the shape-memory support member extends proximally of the distal assembly into the elongated shaft approximately 25 millimeters.

33. The catheter of claim 25, wherein the support member is a nitinol wire having a cross-section with a width of between approximately 0.006 and 0.012 inches.

34. The catheter of claim 25, wherein each of the at least two irrigated ablation ring electrodes has an outer diameter of 2 mm at a middle of the electrode and an outer diameter of 1.7 mm at each of two ends of the electrode.

* * * * *